US006444641B1

(12) United States Patent
Flora

(10) Patent No.: US 6,444,641 B1
(45) Date of Patent: Sep. 3, 2002

(54) FATTY ACID-ACYLATED INSULIN ANALOGS

(75) Inventor: David Benjamin Flora, Greenfield, IN (US)

(73) Assignee: Eli Lilly Company, Indianapolis, IN (US)

( * ) Notice: Subject to any disclaimer, the term of this patent is extended or adjusted under 35 U.S.C. 154(b) by 0 days.

(21) Appl. No.: 09/530,038

(22) PCT Filed: Oct. 22, 1998

(86) PCT No.: PCT/US98/22313
§ 371 (c)(1),
(2), (4) Date: Jul. 7, 2000

(87) PCT Pub. No.: WO99/21573
PCT Pub. Date: May 6, 1999

Related U.S. Application Data

(60) Provisional application No. 60/063,104, filed on Oct. 24, 1997, and provisional application No. 60/088,930, filed on Jun. 11, 1998.

(51) Int. Cl.[7] .................. A61K 38/00; A61K 38/28; C07K 5/00; C07K 7/00
(52) U.S. Cl. ................. 514/3; 514/12; 530/300; 530/303; 530/324; 424/185.1
(58) Field of Search ............ 514/3, 12; 530/300, 530/303, 324; 424/185.1

(56) References Cited

U.S. PATENT DOCUMENTS

| | | | |
|---|---|---|---|
| 4,608,364 A | 8/1986 | Grau | 514/4 |
| 4,701,440 A | 10/1987 | Grau | 514/3 |
| 4,946,828 A | 8/1990 | Markussen | 514/3 |
| 5,015,728 A | 5/1991 | Obermeier et al. | 530/303 |
| 5,491,216 A | 2/1996 | Hoffman et al. | 530/303 |
| 5,506,202 A | 4/1996 | Vertesy et al. | 514/3 |
| 5,646,242 A | 7/1997 | Baker et al. | 530/303 |
| 5,656,722 A | 8/1997 | Dorschug | 530/303 |
| 5,693,609 A | 12/1997 | Baker et al. | 514/3 |
| 5,750,497 A | 5/1998 | Havelund et al. | 514/3 |
| 6,011,007 A | 1/2000 | Havelund et al. | 514/3 |
| 6,051,551 A | 4/2000 | Hughes et al. | 514/3 |
| 6,268,335 B1 | 7/2001 | Brader | 514/3 |
| 6,335,316 B1 | 1/2002 | Hughes et al. | 514/3 |
| 2001/0041786 A1 | 11/2001 | Brader et al. | 530/300 |

FOREIGN PATENT DOCUMENTS

| | | | |
|---|---|---|---|
| JP | 1-254 699 | 10/1989 | C07K/99/26 |
| WO | WO 92/01476 | 2/1992 | |
| WO | WO 95/07931 | 3/1995 | |
| WO | WO 96/29342 | 9/1996 | |

OTHER PUBLICATIONS

Hashimoto et al Synthesis of Palmitoyl Derivatives of Insulin and Their Biological Activities Pharmaceutical Research vol. 6 No. 2 (1989).

Primary Examiner—Christopher S. F. Low
Assistant Examiner—Abdel A. Mohamed
(74) Attorney, Agent, or Firm—Grant E. Reed; Lynn D. Apelgren; James J. Kelley

(57) ABSTRACT

Fatty acid-acylated insulin analogs are soluble at moderately acidic pH and provide long-acting basal control of glucose levels. In such a molecule, the insulin analog portion comprises an insulin A-chain, or an analog thereof, properly cross-linked to an analog of the insulin B-chain, wherein the $\epsilon$-amino group of a Lys residue at either positions 28 or 29 of the B-chain analog is acylated with a fatty acid. The insulin analog portion of the molecules comprises an A-chain of insulin, or an analog thereof, with an optional Arg at position 0, properly cross-linked to a B-chain analog that includes Arg at positions 31 and 32.

39 Claims, 5 Drawing Sheets

Solubility of C14(B29)Gly(A21)tri-Arg Human Insulin as Determined by HPLC

Solubility of C14(B29)Gly(A21)tri-Arg Human Insulin as Determined by HPLC

FATTY ACID-ACYLATED INSULIN ANALOGS

This application claims priority to U.S. Provisional Application Ser. No. 60/063,104, filed on Oct. 24, 1997 and U.S. Provisional Application Ser. No. 60/088,930, filed on Jun. 11, 1998, and is a 371 application of PCT/U.S. 98/22313 filed Oct. 22, 1998.

FIELD OF THE INVENTION

This invention is in the field of clinical medicine and provides fatty acid-acylated insulin analogs with shifted isoelectric points useful for the treatment of diabetes and hyperglycemia.

BACKGROUND OF THE INVENTION

The availability of insulin replacement therapy has prevented the mortality and morbidity of acute complications in diabetes mellitus. However, chronic diabetic complications remain a major health problem due to persistent metabolic derangement, arising principally from poor control of blood glucose. Results emerging from the Diabetes Control and Complications Trial (DCCT) indicate that a decrease of 1% in HbAic (glycosylated hemoglobin) correlates with more than 35% improvement in the incidence of retinopathy [The DCCT Research Group, *New. Engl. J. Med.*, 329, 977–986 (1993)].

In order to achieve normal glycemia, therapy must be designed to parallel as closely as possible the pattern of endogenous insulin secretion in normal individuals. The daily physiological demand for insulin fluctuates and can be separated into two phases: (a) the absorptive phase, which requires a pulse of insulin to dispose of the meal-related blood glucose surge, and (b) the post-absorptive phase, which requires a sustained amount of insulin to regulate hepatic glucose output for maintaining optimal fasting blood glucose. Accordingly, effective therapy involves the combined use of two types of exogenous insulin: a fast-acting meal-time insulin and a long-acting or intermediate-acting basal insulin.

The presently available long-acting or intermediate-acting basal insulins are suspensions which are not ideal in at least two respects. First, the degree of resuspension achieved by patients has been observed to be quite variable. This variable degree of resuspension increases the risk that the patient will withdraw and inject either too much insulin, or too little insulin. [Skyler, J. S., *Medical Clinics of North America*, 72, 1337–1354 (1988)]. If too much insulin is injected, the patient faces an increased risk of hypoglycemia, and its attendant perils of fainting, convulsions, and coma. If too little insulin is injected, the patient's blood glucose level remains higher than desired, which increases the tendency to develop the degenerative vascular consequences of diabetes.

Second, many of these existing insulin formulations for long-acting or intermediate-acting basal glucose control are immunogenic. Beef insulin differs from human insulin at three positions, and long-term use of beef insulin (Ultralente) causes formation of neutralizing antibodies in some people with diabetes. Protamine is a fish protein which has been shown to cause antibody formation in some patients [Ellerhorst, J. A., et al., *The American Journal of the Medical Sciences*, 299, 298–301 (1987)]. Thus, long-term use of beef Ultralente or insulin- NPH formulations carries an increased risk that the patient will become allergic to the insulin formulation, or that antibodies will alter the pharmacokinetics, especially of short-acting insulins. Such consequences may require the patient to stop using these insulin formulations.

Two alternative approaches have been pursued to minimize or avoid these problems. In the first approach, appropriate amino acid modifications are made to raise the isoelectric point of the insulin analog molecule to approximately that of the subcutaneous site. Such insulin analogs remain soluble in the vial because they are formulated at a pH well below their isoelectric points, namely, in the range of pH 3–5. After subcutaneous injection, quick adjustment to physiological pH causes these analogs to precipitate or crystallize. After that, their slow dissolution provides the desired delay in action. Certain insulin analogs are soluble at pH 3–5, yet have prolonged time-action compared with human insulin because they precipitate at higher physiological pH. See, for example, Markussen, J., et al., *Protein Engineering*, 1, 215–223 (1987); Jorgensen, S., et al., *British Medical Journal*, 299, 415–419 (1989); Markussen, J., U.S. Pat. No. 4,946,828, issued Aug. 7, 1990; Zeuzem, S., et al., *Diabetologia*, 33, 65–71 (1990); Vertesy, L., et al., U.S. Pat. No. 5,506,202, issued Apr. 9, 1996; Hofftnann, J., et al., U.S. Pat. No. 5,491,216, issued Feb. 13 1996; Dörschug, M., U.S. Pat. No. 5,656,722, issued Aug. 12, 1997; Chance, R.

E., et al., U.S. Provisional Application Serial. No. 60/055, 828, filed Aug. 15, 1997. While the first approach has provided some interesting results, several problems remain in this area of insulin research.

A second general alternate approach to providing basal control of blood glucose has been to acylate insulin with fatty acids, and to rely on the binding of fatty acids by serum albumin to retain insulin activity in the circulation for extended periods of time [Walder, et al., WO 92/01476; Muranishi, et al., Japanese Patent Application 1–254,699; Hashimoto, M., et al., *Pharmaceutical Research*, 6, 171–176 (1989); Baker, J. C., et al., U.S. Pat. No. 5,693,609, issued Dec. 2, 1997; Havelund, S., et al., WO95/07931, published Mar. 23, 1995; and Jonassen, I., et al., WO96/29342, published Sep. 26, 1996]. While providing some extension, the time-action of these acylated insulins and insulin analogs is not sufficiently long to provide an ideal basal control of blood glucose levels. In particular, they are required to be administered at least two times per day, whereas an ideal basal insulin would only require one administration per day. Furthermore, because certain of the acylated insulins suffer from low potency relative to insulin, significantly greater amounts of these acylated insulins are required to obtain adequate control of blood glucose levels.

SUMMARY OF THE INVENTION

The present invention provides a fatty acid-acylated insulin analog having an isoelectric point that is higher than the isoelectric point of insulin, comprising an insulin analog to which a fatty acyl chain is joined by an amide bond. None of the many publications mentioned above disclose acylated insulin analogs that have increased isoelectric points, and none has suggested their desirability. Acylation of insulin analogs that have increased isoelectric points, relative to insulin, is associated with excellent blood glucose control and provides basal insulin levels that are unexpectedly desirable therapeutically.

The invention further provides a soluble formulation comprising a fatty acid-acylated insulin analog of the present invention, together with one or more excipients selected from a preservative, a metal ion, an isotonicity agent, and a pharmaceutically-acceptable buffer. The invention also provides a method of treating hyperglycemia comprising administering to a patient in need thereof an effective dose of the fatty acid-acylated insulin analog of the present invention. The invention also provides a method of treating hyperglycemia comprising administering to a patient in need thereof an effective dose of the fatty acid-acylated insulin analog of the present invention.

The present invention includes a fatty acid-acylated insulin analog having an isoelectric point that is higher than the isoelectric point of insulin, comprising an insulin analog with a fatty acyl chain bonded to the insulin analog by an amide bond. The present invention also includes a fatty acid-acylated insulin analog having an isoelectric point that is higher than the isoelectric point of insulin, wherein the acylated insulin analog has at least one more net positive charge than insulin. The invention also includes a fatty acid-acylated insulin analog having an isoelectric point that is higher than the isoelectric point of insulin, wherein the acylated insulin analog has at least two more net positive charges than insulin.

The present invention encompasses a mono-acylated insulin analog having the formula below, comprising:

(a) a polypeptide of SEQ ID NO:1 properly crosslinked to a polypeptide of SEQ ID NO:2, or a pharmaceutically acceptable salt thereof, wherein the polypeptide of SEQ ID NO:1 has the sequence:

```
0   1                 5                  10                  15
Xaa Gly Ile Val Glu Gln Cys Cys Thr Ser Ile Cys Ser Leu Tyr Gln Leu   (SEQ ID NO:1)

20
Glu Asn Tyr Cys Xaa
``` wherein:
  Xaa at position 0 is either Arg or absent; and
  Xaa at position 21 is any naturally occurring amino acid except Cys and Lys; and
the polypeptide of SEQ ID NO:2 has the sequence:

```
1                 5                  10                  15
Phe Val Xaa Gln His Leu Cys Gly Ser His Leu Val Glu Ala Leu Tyr   (SEQ ID NO:2)

20                  25                  30
Leu Val Cys Gly Glu Arg Gly Phe Phe Tyr Xaa Xaa Xaa Xaa Arg Arg
``` wherein:
  Xaa at position 3 is any naturally occurring amino acid except Cys and Lys;
  Xaa at position 27 is either Thr or absent;
  Xaa at position 28 is selected from the group consisting of Pro, Leu, Val, Ala, Lys, and Asp;
  Xaa at position 29 is selected from the group consisting of Pro and Lys;
  Xaa at position 30 is absent or any naturally occurring amino acid except Cys or Lys;
  further wherein position 28 or position 29 is Lys, and if position 28 is Lys, position 29 is not Lys; and
(b) Lys at position 28 or position 29 of SEQ ID NO:2 is acylated.

The invention further comprises a the following mono-acylated insulin analogs of the formula above, wherein: Xaa at position 30 of the polypeptide of SEQ ID NO:2 is Thr; wherein Xaa at position 21 of the polypeptide of SEQ ID NO:1 is Asn; or wherein Xaa at position 3 of the polypeptide of SEQ ID NO:2 is Asn.

The invention further comprises a mono-acylated insulin analog of the formula above, wherein Xaa at position 21 of the polypeptide of SEQ ID NO:1 is Asn, and wherein Xaa at position 3 of the polypeptide of SEQ ID NO:2 is Asn. The invention further comprises a mono-acylated insulin analog of the formula above, wherein Xaa at position 21 of the polypeptide of SEQ ID NO:1 is Asn, and wherein Xaa at position 3 of the polypeptide of SEQ ID NO:2 is Asn, and further wherein Xaa at position 28 of the polypeptide of SEQ ID NO:2 is Pro, and Xaa at position 29 of the poiypeptide of SEQ ID NO:2 is Lys. Another monoacylated insulin analog of the invention has the formula above, wherein Xaa at position 21 of the polypeptide of SEQ ID NO:1 is Asn, and wherein Xaa at position 3 of the polypeptide of SEQ ID NO:2 is Asn, and further wherein Xaa at position 28 of the polypeptide of SEQ ID NO:2 is Lys, and Xaa at position 29 of the polypeptide of SEQ ID NO:2 is Pro.

The invention also includes a mono-acylated insulin analog of the formula above, wherein Xaa at position 21 of the polypeptide of SEQ ID NO:1 is Gly, and Xaa at position 3 of the polypeptide of SEQ ID NO:2 is Gin. Still another analog as the formula above, wherein Xaa at position 21 of the polypeptide of SEQ ID NO:1 is Gly, and Xaa at position 3 of the polypeptide of SEQ ID NO:2 is Asp.

The invention further comprises a mono-acylated insulin analog of the formula above, wherein the Lys at position 28 or position 29 of the polypeptide of SEQ ID NO:2 is acylated with a $C_4$–$C_{21}$ fatty acid. The invention also includes mono-acylated insulin analog of the formula above, wherein the Lys at position 28 or position 29 of the polypeptide of SEQ ID NO:2 is acylated with a $C_{10}$–$C_{18}$ fatty acid. The invention also includes a mono-acylated insulin analog of the formula above, wherein the Lys at position 28 or position 29 of the polypeptide of SEQ ID NO:2 is acylated with a fatty acid selected from the group consisting of palmitic and myristic acid.

The invention further comprises a mono-acylated insulin analog of the formula above, wherein the Lys at position 28 or position 29 of the polypeptide of SEQ ID NO:2 is acylated with a $C_4$–$C_8$ fatty acid. The invention additionally comprises a mono-acylated insulin analog of the formula above, wherein the Lys at position 28 or position 29 of the polypeptide of SEQ ID NO:2 is acylated with a fatty acid selected from the group consisting of octanoic and hexanoic acid.

Yet another analog has the formula above, wherein Xaa at position 0 of the polypeptide of SEQ ID NO:1 is Arg, which is a mono-acylated tri-arginine insulin analog. The invention comprises modifications of this tri-arginine insulin analog, such as an analog wherein Xaa at position 21 of the polypeptide of SEQ ID NO:1 is selected from the group consisting of Gly, Asn, Ala, and Gln. Another tri-arginine insulin analog has Xaa at position 21 of the polypeptide of SEQ ID NO:1 is Gly. Yet another tri-arginine insulin analog has Xaa at position 21 of the polypeptide of SEQ ID NO:1 is Asn.

Another mono-acylated tri-arginine insulin analog of the invention has the formula above, wherein Xaa at position 21 of the polypeptide of SEQ ID NO:1 is Gly, Xaa at position 3 of SEQ ID NO:2 is Asn; Xaa at position 27 of SEQ ID NO:2 is Thr; Xaa at position 28 of SEQ ID NO:2 is Pro; and Xaa at position 29 of SEQ ID NO:2 is Lys. Yet another mono-acylated tri-arginine insulin analog of the invention has the formula above, wherein Xaa at position 21 of the polypeptide of SEQ ID NO:1 is Gly, Xaa at position 3 of SEQ ID NO:2 is Gln; Xaa at position 27 of SEQ ID NO:2 is Thr; Xaa at position 28 of SEQ ID NO:2 is Pro; and Xaa at position 29 of SEQ ID NO:2 is Lys.

Still another mono-acylated tri-arginine insulin analog of the invention has the formula above, wherein Xaa at position 21 of the polypeptide of SEQ ID NO:1 is Gly, Xaa at position 3 of SEQ ID NO:2 is Asp; Xaa at position 27 of SEQ ID NO:2 is Thr; Xaa at position 28 of SEQ ID NO:2 is Pro; and Xaa at position 29 of SEQ ID NO:2 is Lys. Yet another mono-acylated tri-arginine insulin analog of the invention has the formula above, wherein Xaa at position 21 of the polypeptide of SEQ ID NO:1 is Asn, Xaa at position 3 of SEQ ID NO:2 is Asn; Xaa at position 27 of SEQ ID NO:2 is Thr, and Xaa at position 28 of SEQ ID NO:2 is Pro, and Xaa at position 29 of SEQ ID NO:2 is Lys.

The invention also encompasses a mono-acylated tri-arginine insulin analog of the formula above, wherein Xaa at position 21 of the polypeptide of SEQ ID NO:1 is Gly, Xaa at position 3 of SEQ ID NO:2 is Asn; Xaa at position 27 of SEQ ID NO:2 is Thr; Xaa at position 28 of SEQ ID NO:2 is Lys; and Xaa at position 29 of SEQ ID NO:2 is Pro. Still another mono-acylated tri-arginine insulin analog of the invention has the formula above, wherein Xaa at position 21 of the polypeptide of SEQ ID NO:1 is Gly, Xaa at position 3 of SEQ ID NO:2 is Gln; Xaa at position 27 of SEQ ID NO:2 is Thr; Xaa at position 28 of SEQ ID NO:2 is Lys; and Xaa at position 29 of SEQ ID NO:2 is Pro.

The invention includes yet another mono-acylated tri-arginine insulin analog of the formula above, wherein Xaa at position 21 of the polypeptide of SEQ ID NO:1 is Gly, Xaa at position 3 of SEQ ID NO:2 is Asp; Xaa at position 27 of SEQ ID NO:2 is Thr; Xaa at position 28 of SEQ ID NO:2 is Lys; and Xaa at position 29 of SEQ ID NO:2 is Pro. The invention also comprises a mono-acylated tri-arginine insulin analog of the formula above, wherein Xaa at position 21 of the polypeptide of SEQ ID NO:1 is Asn, Xaa at position 3 of SEQ ID NO:2 is Asn; Xaa at position 27 of SEQ ID NO:2 is Thr; Xaa at position 28 of SEQ ID NO:2 is Lys; and Xaa at position 29 of SEQ ID NO:2 is Pro.

Yet another analog has the formula above, wherein Xaa at position 0 of the polypeptide of SEQ ID NO:1 is absent, which is a mono-acylated di-arginine insulin analog. An analog of the invention is a mono-acylated di-arginine insulin analog having the formula above, wherein Xaa at position 21 of the polypeptide of SEQ ID NO:1 is selected from the group consisting of Gly, Asn, Ala, and Gln.

The invention also includes a mono-acylated di-arginine insulin analog having the formula above, wherein Xaa at position 21 of the polypeptide of SEQ ID NO:1 is Gly. The invention also includes a mono-acylated di-arginine insulin analog having the formula above, wherein Xaa at position 21 of the polypeptide of SEQ ID NO:1 is Asn.

The invention also includes a mono-acylated di-arginine insulin analog having the formula above, wherein Xaa at position 21 of the polypeptide of SEQ ID NO:1 is Gly, Xaa at position 3 of SEQ ID NO:2 is Asn; Xaa at position 27 of SEQ ID NO:2 is Thr; Xaa at position 28 of SEQ ID NO:2 is Pro; and Xaa at position 29 of SEQ ID NO:2 is Lys. The invention also includes a mono-acylated di-arginine insulin analog having the formula above, wherein Xaa at position 21 of the polypeptide of SEQ ID NO:1 is Gly, Xaa at position 3 of SEQ ID NO:2 is Gln; Xaa at position 27 of SEQ ID NO:2 is Thr; Xaa at position 28 of SEQ ID NO:2 is Pro; and Xaa at position 29 of SEQ ID NO:2 is Lys.

The invention also includes a mono-acylated di-arginine insulin analog having the formula above, wherein Xaa at position 21 of the polypeptide of SEQ ID NO:1 is Asn, Xaa at position 3 of SEQ ID NO:2 is Asn; Xaa at position 27 of SEQ ID NO:2 is Thr; Xaa at position 28 of SEQ ID NO:2 is Pro; and Xaa at position 29 of SEQ ID NO:2 is Lys. The invention further includes a mono-acylated di-arginine insulin analog having the formula above, wherein Xaa at position 21 of the polypeptide of SEQ ID NO:1 is Gly, Xaa at position 3 of SEQ ID NO:2 is Asn; Xaa at position 27 of SEQ ID NO:2 is Thr; Xaa at position 28 of SEQ ID NO:2 is Lys; and Xaa at position 29 of SEQ ID NO:2 is Pro.

The invention also includes a mono-acylated di-arginine insulin analog having the formula above, wherein Xaa at position 21 of the polypeptide of SEQ ID NO:1 is Gly, Xaa at position 3 of SEQ ID NO:2 is Gln; Xaa at position 27 of SEQ ID NO:2 is Thr; Xaa at position 28 of SEQ ID NO:2 is Lys; and Xaa at position 29 of SEQ ID NO:2 is Pro. The invention also includes a mono-acylated di-arginine insulin analog having the formula above, wherein Xaa at position 21 of the polypeptide of SEQ ID NO:1 is Asn, Xaa at position 3 of SEQ ID NO:2 is Asn; Xaa at position 27 of SEQ ID NO:2 is Thr; Xaa at position 28 of SEQ ID NO:2 is Lys; and Xaa at position 29 of SEQ ID NO:2 is Pro.

The invention includes the following inventive monoacylated insulin analogs: B29-N$^\epsilon$-Gly$^{A21}$Arg$^{B31}$Arg$^{B32}$-myristoyl human insulin; B29-N$^\epsilon$-Gly$^{A21}$Gln$^{B3}$Arg$^{B31}$Arg$^{B32}$-myristoyl human insulin; B29-N$^\epsilon$-Arg$^{A0}$Gly$^{A21}$Arg$^{B31}$Arg$^{B32}$-myristoyl human insulin; B29-N$^\epsilon$-Arg$^{A0}$Gly$^{A21}$Gln$^{B3}$Arg$^{B31}$Arg$^{B32}$-myristoyl human insulin; B29-N$^\epsilon$-Arg$^{A0}$Gly$^{A21}$Asp$^{B3}$Arg$^{B31}$Arg$^{B32}$-myristoyl human insulin; B29-N$^\epsilon$-Arg$^{B31}$Arg$^{B32}$-myristoyl human insulin; B29-N$^\epsilon$-Arg$^{A0}$Arg$^{B31}$Arg$^{B32}$-myristoyl human insulin analog; B29-N$^\epsilon$-Gly$^{A21}$Arg$^{B31}$Arg$^{B32}$-octanoyl human insulin; B29-N$^\epsilon$-Gly$^{A21}$Gln$^{B3}$Arg$^{B31}$Arg$^{B32}$-octanoyl human insulin; B29-N$^{\epsilon\text{-}ArgA0}$Gly$^{A21}$Arg$^{B31}$Arg$^{B32}$-octanoyl human insulin; B29-N$^\epsilon$-Arg$^{A0}$Gly$^{A21}$Gln$^{B3}$Arg$^{B31}$Arg$^{B32}$-octanoyl human insulin;B29-N$^{\epsilon\text{-}ArgA0}$Gly$^{A21}$ Asp$^{B3}$Arg$^{B31}$Arg$^{B32}$-octanoyl human insulin; B29-N$^\epsilon$-Arg$^{B31}$Arg$^{B32}$-octanoyl human insulin; B29-N$^\epsilon$-Arg$^{A0}$Arg$^{B31}$Arg$^{B32}$-octanoyl human insulin analog; -N$^\epsilon$-Gly$^{A21}$Lys$^{B28}$Pro$^{B29}$Arg$^{B31}$Arg$^{B32}$-myristoyl human insulin; B28-N$^\epsilon$-Gly$^{A21}$Gln$^{B3}$Lys$^{B28}$Pro$^{B29}$Arg$^{B31}$Arg$^{B32}$-myristoyl human insulin; B28-N$^\epsilon$-Arg$^{A0}$Gly$^{A21}$Lys$^{B28}$Pro$^{B29}$Arg$^{B31}$Arg$^{B32}$-myristoyl human insulin; B28-N$^\epsilon$-Arg$^{A0}$Gly$^{A21}$Gln$^{B3}$Lys$^{B28}$Pro$^{B29}$Arg$^{B31}$Arg$^{B32}$-myristoyl human insulin; B28-N$^\epsilon$-Arg$^{A0}$Gly$^{A21}$Asp$^{B3}$Lys$^{B28}$Pro$^{B29}$Arg$^{B31}$Arg$^{B32}$-myristoyl human insulin; B28-N$^\epsilon$-Lys$^{B28}$Pro$^{B29}$Arg$^{B31}$Arg$^{B32}$-myristoyl human insulin; B28-N$^\epsilon$-Arg$^{A0}$Lys$^{B28}$Pro$^{B29}$Arg$^{B31}$Arg$^{B32}$-myristoyl human insulin; B28-N$^\epsilon$-Gly$^{A21}$Lys$^{B28}$Pro$^{B29}$Arg$^{B31}$Arg$^{B32}$-octanoyl human insulin; B28-N$^\epsilon$-Gly$^{A21}$Gln$^{B3}$Lys$^{B28}$Pro$^{B29}$Arg$^{B31}$Arg$^{B32}$-octanoyl human insulin; B28-N$^\epsilon$-Arg$^{A0}$Gly$^{A21}$Lys$^{B28}$Pro$^{B29}$Arg$^{B31}$Arg$^{B32}$-octanoyl human insulin; B28-N$^\epsilon$-

Arg$^{A0}$Gly$^{A21}$Gln$^{B3}$Lys$^{B28}$Pro$^{B29}$Arg$^{B31}$Arg$^{B32}$-octanoyl human insulin; B28-N$^\epsilon$-Arg$^{A0}$Gly$^{A21}$Asp$^{B3}$Lys$^{B28}$Pro$^{B29}$Arg$^{B31}$Arg$^{B32}$-octanoyl human insulin; B28-N$^\epsilon$-Lys$^{B28}$Pro$^{B29}$Arg$^{B31}$Arg$^{B32}$-octanoyl human insulin; B28-N$^\epsilon$-Arg$^{A0}$Lys$^{B28}$Pro$^{B29}$Arg$^{B31}$Arg$^{B32}$-octanoyl human insulin.

The invention also encompasses various formulations comprising any of the above-described mono-acylated insulin analogs. Such a formulation may comprise a preservative, such as m-cresol or phenol, an isotonicity agent, a pharmaceutically-acceptable buffer, and/or a metal in the +2 oxidation state, such as cobalt or zinc. The invention also includes a formulation comprising a mono-acylated insulin analog of the invention with a pH of between about 3.0 to about 3.8. The invention also includes a formulation comprising a mono-acylated insulin analog of the invention with a pH of about 3.5.

The invention further comprises a formulation comprising a mono-acylated insulin analog of the invention with a pH of between about 4.5 and 7.6. The invention additionally includes a formulation comprising a mono-acylated insulin analog of the invention, with a pH of between about 5.0 and about 7.0. The invention further includes a formulation comprising a mono-acylated insulin analog of the invention, with a pH of about 6.5.

The invention includes therapeutic methods, comprising administering to a patient suffering from diabetes, a formulation comprising a mono-acylated insulin analog of the invention. In particular, any of the above-recited mono-acylated insulin analogs of the invention are suitable for such therapeutic methods. The formulation administered in the inventive therapeutic method may have a pH of between about 3.0 to about 3.8 or a pH of about 3.5. The formulation administered in the therapeutic method may also have a pH of between about 4.5 and 7.6, or between about 5.0 and about 7.0, or the formulation may have a pH of about 6.5.

DETAILED DESCRIPTION OF THE INVENTION

Definitions

Figure 1:
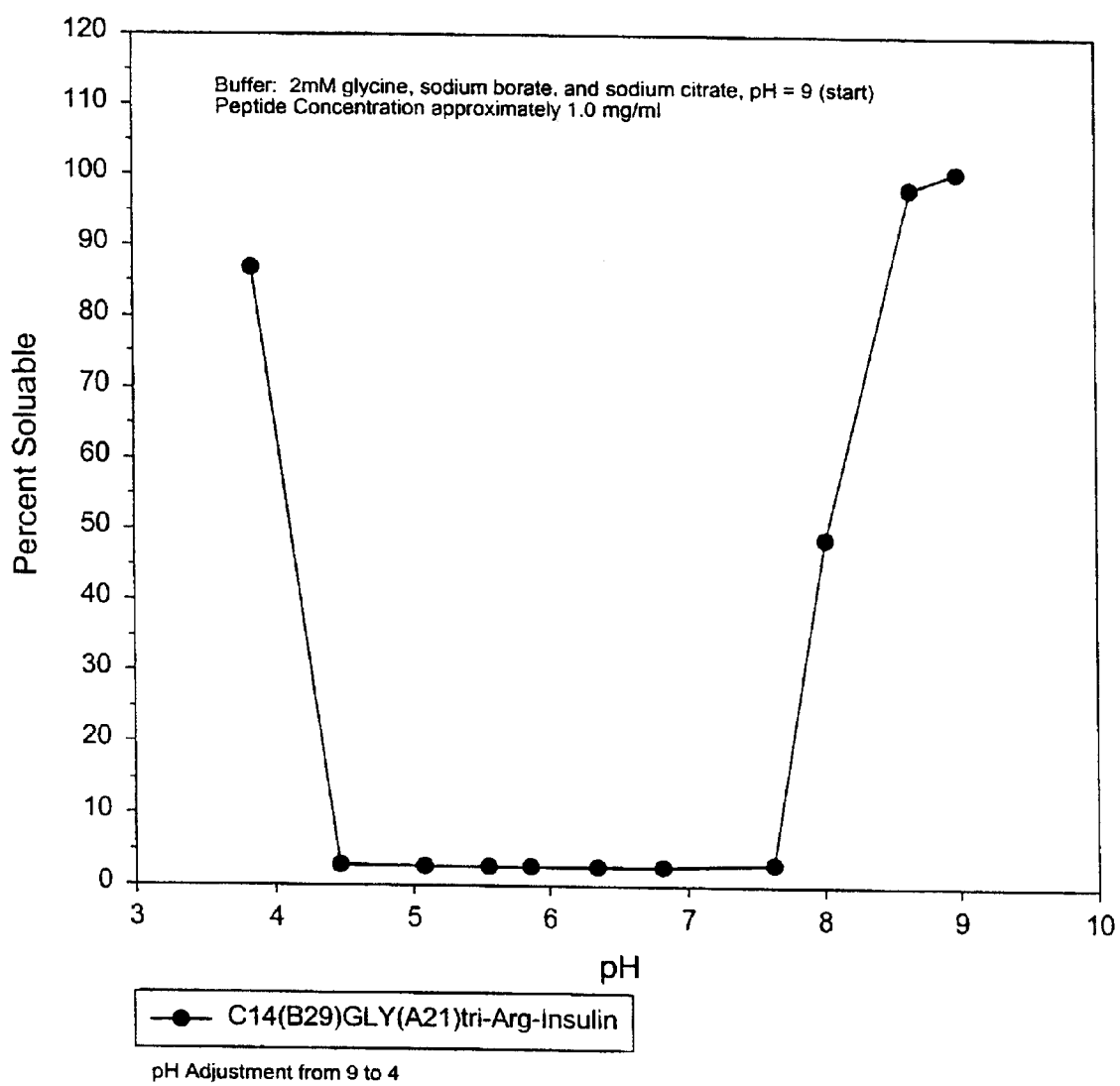
FIG. 1 is a graph showing the solubility of B29-N$^\epsilon$-Arg$^{A0}$Gly$^{A21}$Arg$^{B31}$Arg$^{B32}$-myristoyl human insulin analog as a function of pH.

An "amino acid modification" or a "modification" is a deletion or removal of an amino acid, a replacement of one amino acid for another, an insertion of an amino acid at an internal position, or an addition of an amino acid to one of the termini. An amino acid modification also includes a derivatization of an amino acid such as acylation of an amino group.

The term "insulin" as used herein, refers to human insulin, whose amino acid sequence and spatial structure are well-known. Human insulin is comprised of a twenty-one amino acid A-chain and a thirty amino acid B-chain which are cross-linked by disulfide bonds. A properly cross-linked insulin contains three disulfide bridges: one between position 7 of the A-chain and position 7 of the B-chain, a second between position 20 of the A-chain and position 19 of the B-chain, and a third between positions 6 and 11 of the A-chain [Nicol, D. S. H. W. and Smith, L. F., *Nature*, 187, 483–485 (1960)].

The term "insulin analog" means a protein that has an A-chain and a B-chain that have substantially the same amino acid sequences as the A-chain and/or B-chain of human insulin, respectively, but differ from the A-chain and B-chain of human insulin by having one or more amino acid deletions, one or more amino acid replacements, and/or one or more amino acid additions that do not destroy the insulin activity of the insulin analog. An insulin analog having an isoelectric point that is "higher than" the isoelectric point of insulin is one type of insulin analog. Another type of insulin analog is a "monomeric insulin analog."

A "monomeric insulin analog" is a fast-acting analog of human insulin, including, for example, human insulin wherein Pro at position B28 is substituted with Asp, Lys, Leu, Val, or Ala, and wherein Lys at position B29 is Lys or is substituted with Pro. Another monomeric insulin analog, also known as des(B27) human insulin, is human insulin wherein Thr at position 27 of the B-chain is deleted. Monomeric insulin analogs are disclosed in Chance, R. E., et al., U.S. Pat. No. 5,514,646, issued May 7, 1996; Brems, D. N., et al. *Protein Engineering*, 5, 527–533 (1992); Brange, J. J. V., et al., EPO publication No. 214,826 (published March 18, 1987); and Brange, J. J. V., et al., *Current Opinion in Structural Biology*, 1, 934–940 (1991). The monomeric insulin analogs employed in the present formulations are properly cross-linked at the same positions as in human insulin.

SEQ ID NO:1 refers to an insulin A-chain, or an analog thereof, having the amino acid sequence:

```
 0   1              5                   10                  15
Xaa Gly Ile Val Glu Gln Cys Cys Thr Ser Ile Cys Ser Leu Tyr Gln Leu   (SEQ ID NO:1)

20
Glu Asn Tyr Cys Xaa
``` wherein:

Xaa at position 0 is either Arg or absent; and

Xaa at position 21 is any naturally occurring amino acid except Cys and Lys.

SEQ ID NO:2 refers to the insulin B-chain analog having the amino acid sequence:

```
 1               5                   10                  15
Phe Val Xaa Gln His Leu Cys Gly Ser His Leu Val Glu Ala Leu Tyr   (SEQ ID NO:2)

20                  25                  30
Leu Val Cys Gly Glu Arg Gly Phe Phe Tyr Xaa Xaa Xaa Xaa Arg Arg
``` wherein:

Xaa at position 3 is any naturally occurring amino acid except Cys or Lys;

Xaa at position 27 is either Thr or absent;

Xaa at position 28 is Pro, Leu, Val, Ala, Asp, or Lys;

Xaa at position 29 is Pro or Lys;

Xaa at position 30 is absent or any naturally occurring amino acid except Cys or Lys; and further wherein position 28 or position 29 is Lys, and if position 28 is Lys, position 29 is not Lys.

The insulin analogs of the present invention comprise the polypeptide of SEQ ID NO:1 properly cross-linked to the polypeptide of SEQ ID NO:2. Furthermore, the insulin analogs of the present invention are acylated with a fatty acid at the ε-amino group of the Lys residue at position 28 or position 29 of the B-chain defined by SEQ ID NO:2.

The term "naturally occurring amino acid" refers to amino acids that are normally found in polypeptides found in the human organism. Examples of naturally occurring amino acids include: Ala, Arg, Asn, Asp, Cys, Gln, Glu, Gly, His, lie, Leu, Lys, Met, Phe, Pro, Ser, Thr, Trp, Tyr, and Val. Where the phrase "any naturally occurring amino acid except Cys or Lys" is used it refers to the above list of amino acids with Cys and Lys removed from the list.

The term "cross-link" refers to disulfide bonds between cysteine residues. A "properly cross-linked" human insulin, monomeric insulin analog, insulin analog, or proinsulin-like precursor contains three disulfide bridges. One disulfide bridge joins the cysteine residues at positions 6 and 11 of the A-chain. A second disulfide bridge joins the cysteine residue at position 7 of the A-chain with the cysteine at position 7 of the B-chain. A third disulfide bridge joins the cysteine at position 20 of the A-chain to the cysteine at position 19 of the B-chain.

The term "tri-arginine insulin analog" refers to an analog of human insulin with Arg at position 0 of the A-chain as set forth in SEQ ID NO:1 and Arg at both positions 31 and 32 of the B-chain as set forth in SEQ ID NO:2. The term "tri-arginine" may be abbreviated as "tri-arg."

The term "di-arginine insulin analog" refers to an analog of human insulin with Arg at both positions 31 and 32 of the B-chain as set forth in SEQ ID NO:2. The term "di-arginine" may be abbreviated as "di-arg."

The verb "acylate" means to form the amide bond between a fatty acid and an amino group of a protein. An insulin is "acylated" when one or more of its amino groups is combined in an amide bond with the acid group of a fatty acid.

The term "acylating group" refers to the fatty acid chemically bonded to the ε-amino group of the insulin analog. The free amino group of Lys at position B28 or B29 of SEQ ID NO:2 is an ε-amino group.

The term "acylating" means the covalent bonding of one or more acyl groups to a free amino group of the protein. The term "selective acylation" means the preferential acylation of the ε-amino group(s) over the α-amino groups.

The term "fatty acid" means a saturated or unsaturated $C_4$–$C_2$, fatty acid. The preferred fatty acids are saturated and include $C_{10}$–$C_{18}$ acids including myristic acid ($C_{14}$), pentadecylic acid ($C_{15}$), palmitic acid ($C_{16}$), heptadecylic acid ($C_{17}$) and stearic acid ($C_{18}$). In this group, the most preferable fatty acids include myristic and paimitic acid. Other preferred fatty acids of the present invention include $C_4$–$C_8$ acids including butanoic acid ($C_4$), pentanoic acid ($C_5$), hexanoic acid ($C_6$), heptanoic acid ($C_7$), and octanoic acid ($C_8$). In this group, the most preferred fatty acids include hexanoic and octanoic acid. The compounds of the present invention represent mono-acylated insulin analogs acylated at an ε-amino group with a $C_4$–$C_{21}$, fatty acid. Preferably, the analogs are mono-acylated at the ε-amino group of lysine at position 28 or 29 of the B-Chain.

The term "mono-acylated insulin analog" refers to a protein selected from the group consisting of insulin and insulin analogs that is acylated with a fatty acid that is bonded through an amide bond formed between the acid group of a fatty acid and an amino group of the protein, and pharmaceutically-acceptable salts and complexes thereof. In the present invention, the amino group is the ε-amino group of a Lys residue at position 28 or 29 of the B chain as set forth in SEQ ID NO:2. The acylation of insulin with a fatty acid is disclosed in a Japanese patent application 1-254,699. See also, Hashimoto, M., et al., *Pharmaceutical Research*, 6, 171–176 (1989), and Lindsay, et al., *Biochemical J.*, 121, 737–745 (1971). Further disclosure of fatty acid-acylated insulins and fatty acid-acylated insulin analogs, and of methods for their synthesis, is found in Baker, et al, U.S. Pat. No. 5,693,609, issued Dec. 2, 1997; Havelund, et al., WO95/0793 1, published Mar. 23, 1995; and Jonassen, et al., WO96/29342, published Sep. 26, 1996.

The preferred mono-acylated insulin analogs of the present invention include di-arginine and tri-arginine species. A preferred mono-acylated insulin analog of the present invention has a Thr at position 30 of SEQ ID NO:2. Other preferred mono-acylated insulin analogs of the present invention include tri-arginine and di-arginine species with Gly, Asn, Ala, or Gln at position 21 of SEQ ID NO:1. Particularly preferred, are species with a Gly or Asn at position 21 of SEQ ID NO:1. Still other preferred monoacylated insulin analogs of the present invention include di-arginine and tri-arginine species having Asn at either position 21 of SEQ ID NO:1 or position 3 of SEQ ID NO:2 or at both positions. Another group of preferred mono-acylated insulin analogs of the present invention include tri-arginine species having Gly at position 21 of SEQ ID NO:1 and either Asp or Gln at position 3 of SEQ ID NO:2. Another group of preferred mono-acylated insulin analogs include di-arginine species having Gly at position 21 of SEQ ID NO:1 and Gln at position 3 of SEQ ID NO:2. Finally, other preferred acylated insulin analogs of the present invention include di-arginine and tri-arginine species having Lys at position 28 of SEQ ID NO:2 and Pro at position 29 of SEQ ID NO:2 or Pro at position 28 of SEQ ID NO:2 and Lys at position 29 of SEQ ID NO:2.

Examples of some highly preferred di-arginine and tri-arginine species include those with either Asn or Gly at position 21 of SEQ ID NO:1; Asn at position 3 of SEQ ID NO:2; Thr at position 27 of SEQ ID NO:2; Pro at position 28 of SEQ ID NO:2; and Lys at position 29 of SEQ ID NO:2. Other highly preferred di-arginine and tri-arginine species include those with either Asn or Gly at position 21 of SEQ ID NO:1; Asn at position 3 of SEQ ID NO:2; Thr at position 27 of SEQ ID NO:2; Lys at position 28 of SEQ ID NO:2; and Pro at position 29 of SEQ ID NO:2.

The most highly preferred di-arginine and tri-arginine species include insulin analogs acylated at the $\epsilon$-amino group of a Lys at either position 28 or position 29 of SEQ ID NO:2 where the acylating group is octanoic or myristic acid. Examples of these most preferred monoacylated insulin analogs include:

B29-$N^\epsilon$-Gly$^{A21}$Arg$^{B31}$Arg$^{B32}$-myristoyl human insulin analog;

B29-$N^\epsilon$-Gly$^{A21}$Gln$^{B3}$Arg$^{B31}$Arg$^{B32}$-myristoyl human insulin analog;

B29-$N^\epsilon$-Arg$^{A0}$Gly$^{A21}$Arg$^{B31}$Arg$^{B32}$-myristoyl human insulin analog;

B29-$N^\epsilon$-Arg$^{A0}$Gly$^{A21}$Gln$^{B3}$Arg$^{B31}$Arg$^{B32}$-myristoyl human insulin analog;

B29-$N^\epsilon$-Arg$^{A0}$Gly$^{A21}$Asp$^{B3}$Arg$^{B31}$Arg$^{B32}$-myristoyl human insulin analog;

B29-$N^\epsilon$-Arg$^{B31}$Arg$^{B32}$-myristoyl human insulin analog;

B29-$N^\epsilon$-Arg$^{A0}$Arg$^{B31}$Arg$^{B32}$-myristoyl human insulin analog;

B29-$N^\epsilon$-Gly$^{A21}$Arg$^{B31}$Arg$^{B32}$-octanoyl human insulin analog;

B29-$N^\epsilon$-Gly$^{A21}$Gln$^{B3}$Arg$^{B31}$Arg$^{B32}$-octanoyl human insulin analog;

B29-$N^\epsilon$-Arg$^{A0}$Gly$^{A21}$Arg$^{B31}$Arg$^{B32}$-octanoyl human insulin analog;

B29-$N^\epsilon$-Arg$^{A0}$Gly$^{A21}$Gln$^{B3}$Arg$^{B31}$Arg$^{B32}$-octanoyl human insulin analog;

B29-$N^\epsilon$-Arg$^{A0}$Gly$^{A21}$Asp$^{B3}$Arg$^{B31}$Arg$^{B32}$-octanoyl human insulin analog;

B29-$N^\epsilon$-Arg$^{B31}$Arg$^{B32}$-octanoyl human insulin analog;

B29-$N^\epsilon$-Arg$^{A0}$Arg$^{B31}$Arg$^{B32}$-octanoyl human insulin analog;

B28-$N^\epsilon$-Gly$^{A21}$Lys$^{B28}$Pro$^{B29}$Arg$^{B31}$Arg$^{B32}$-myristoyl human insulin analog;

B28-$N^\epsilon$-Gly$^{A21}$Gln$^{B3}$Lys$^{B28}$Pro$^{B29}$Arg$^{B31}$Arg$^{B32}$-myristoyl human insulin analog;

B28-$N^\epsilon$-Arg$^{A0}$GLy$^{A21}$Lys$^{B28}$Pro$^{B29}$Arg$^{B31}$Arg$^{B32}$-myristoyl human insulin analog;

B28-$N^\epsilon$-Arg$^{A0}$Gly$^{A21}$Gln$^{B3}$Lys$^{B28}$Pro$^{B29}$Arg$^{B31}$Arg$^{B32}$-myristoyl human insulin analog;

B28-$N^\epsilon$-Arg$^{A0}$Gly$^{A21}$Asp$^{B3}$Lys$^{B28}$Pro$^{B29}$Arg$^{B31}$Arg$^{B32}$-myristoyl human insulin analog;

B28-$N^\epsilon$-Lys$^{B28}$Pro$^{B29}$Arg$^{B31}$Arg$^{B32}$-myristoyl human insulin analog;

B28-$N^\epsilon$-Arg$^{A0}$Lys$^{B28}$Pro$^{B29}$Arg$^{B31}$Arg$^{B32}$-myristoyl human insulin analog;

B28-$N^\epsilon$-Gly$^{A21}$Lys$^{B28}$Pro$^{B29}$Arg$^{B31}$Arg$^{B32}$-octanoyl human insulin analog;

B28-$N^\epsilon$-Gly$^{A21}$Gln$^{B3}$Lys$^{B28}$Pro$^{B29}$Arg$^{B31}$Arg$^{B32}$-octanoyl human insulin analog;

B28-$N^{\epsilon\text{-}ArgA0}$Gly$^{A21}$Lys$^{B28}$Pro$^{B29}$Arg$^{B31}$Arg$^{B32}$-octanoyl human insulin analog;

B28-$N^{\epsilon\text{-}ArgA0}$Gly$^{A21}$Gln$^{B3}$Lys$^{28}$Pro$^{B29}$Arg$^{B31}$Arg$^{B32}$-octanoyl human insulin analog;

B28-$N^{\epsilon\text{-}ArgA0}$Gly$^{A21}$Asp$^{B3}$Lys$^{B28}$Pro$^{B29}$Arg$^{B31}$Arg$^{B32}$-octanoyl human insulin analog;

B28-$N^{\epsilon\text{-}LysB28}$Pro$^{B29}$Arg$^{B31}$Arg$^{B32}$-octanoyl human insulin analog; and B28-$N^{\epsilon\text{-}ArgA0}$Lys$^{B28}$Pro$^{B29}$Arg$^{B31}$Arg$^{B32}$-octanoyl human insulin analog.

An insulin analog analog having an isoelectric point that is "higher than" the isoelectric point of insulin refers to an insulin analog wherein a modification or modifications of amino acid sequence compared with insulin result in a higher isoelectric point compared with insulin. The isoelectric point of human insulin is pH 5.4 [Markussen, J., et al., Protein Engineering 1, 205–213 (1987)]. An acylated insulin analog having an isoelectric point higher than that of insulin means an acylated insulin analog wherein the isoelectric point is at least about pH 6.0. Preferably, an acylated insulin analog having an isoelectric point higher than that of insulin has an isoelectric point between about pH 6.0 and about 8.0. More preferably, the isoelectric point of will have a pH between about 6.0 and 7.0. Most preferably, the isoelectric point will have a pH of about 7.0. With respect to the isoelectric points of these analogs, "about" means plus or minus 0.1 pH units. Thus, "about 6.0 " means pH 5.9to pH6.1.

Changes in isoelectric point are achieved, for example, by adding one or more basic amino acids to the sequence, by replacing one or more amino acids in the sequence with a basic amino acid, by removing one or more acidic residues from the sequence, or by replacing one or more acidic amino acids either with uncharged amino acids or with basic amino acids. Certain insulin analogs having an isoelectric point higher than insulin have been disclosed [Markussen, J., et al., Protein Engineering, 1, 215–223 (1987); Jorgensen, S., et al., British Medical Journal, 299, 415–419 (1989); Markussen, J., U.S. Pat. No. 4,946,828, issued Aug. 7, 1990; Zeuzem, S., et al., Diabetologia, 33, 65–71 (1990); Vertesy, L., et al., U.S. Pat. No. 5,506,202, issued Apr. 9, 1996; Hoffmann, J., et al., U.S. Pat. No. 5,491,216, issued Feb. 13, 1996; Dörschug, M., U.S. Pat. No. 5,656,722, issued Aug. 12, 1997; Chance, R. E., et al., U.S. Provisional Application No. 60/055,828, filed Aug. 15, 1997].

Each of the mono-acylated di-arginine and tri-arginine insulin analogs of the present invention has an isoelectric point higher than that of human insulin due to the additional basic Arg residues at positions 31 and 32 of the polypeptide of SEQ ID NO:2 present in each of the species and the Arg residue at position 0 of SEQ ID NO:1 in the tri-arginine insulin analogs. Additionally, each of the di-arginine and tri-arginine species is acylated with a fatty acid at the $\epsilon$-amino group of the Lys residue present at either position 28 or 29 of SEQ ID NO:2. Thus, the present invention is a fatty acid-acylated insulin analog having an isoelectric point higher than the isoelectric point of insulin. It includes an insulin analog with a fatty acyl chain bonded to the insulin analog by an amide bond. Preferred embodiments of the invention include those compounds where the acylated insulin analog has at least one more net positive charge than insulin. Also preferred are those compounds where the acylated insulin analog has at least two more net positive charges than insulin. The unique properties of the compounds of the invention are related to their shifted isoelectric points and attached fatty acid groups. These inventive compounds and pharmaceutical formulations of these insulin analogs exhibit long-lasting basal effects The isoelectric point of a polypeptide is the pH at which there is no net electric charge on a protein. At this pH, the electrophoretic mobility is zero and the molecule will not move in an electrophoresis gel. At a pH below the isoelectric point, the basic groups on amino acids such as Arg, Lys, and His are protonated giving the molecule a positive charge and at a pH higher than the isoelectric point, the carboxylic acid groups on any Glu or Asp residues are deprotonated giving the molecule a negative charge. A polypeptide that is charged either by protonation or deprotonation will be more polar and will necessarily exhibit increased solubility in water compared with the polypeptide at its isoelectric point. Thus, the solubility of a polypeptide in an aqueous system will vary depending on the pH of the system and the isoelectric point of the polypeptide. A shift in the isoelectric point of an insulin analog can greatly effect the solubility of the analog at physiological pH.

The procedure for determining net charge on an insulin, insulin analog, or acylated insulin analog is quite simple. First, the amount of total positive charge is calculated by adding up the number of basic amino acids (Lys, His, and Arg) and treating each as having a positive charge equal to one. Next, the total negative charge is calculated by adding up the number of acidic amino acids (Asp and Glu) and treating each as having a negative charge equal to one. Finally, the total negative charge is subtracted from the total positive charge to give a net charge for an insulin, insulin analog, or acylated insulin analog. These charges are assigned based on the charge of each amino acid at physiological pH. For example, Lys and Arg are given positive charges because at physiological pH their respective basic groups are protonated giving them a positive charge. Although His may be charged or uncharged at physiological pH depending on its local environment, His is given a charge of plus one for the purposes of this discussion. Asp and Glu are assigned negative charges because the free carboxylic acid functionalities of these amino acids are deprotonated at physiological pH giving them a negative charge.

The net charge on human insulin is easily calculated using the above method. For example, the 4 basic amino acids (His at B5, His at B10, Arg at B22, and Lys at B29) give a total positive charge of +4. Similarly, the 4 acidic amino acids (Glu at position A4, Glu at position A17, Glu at position B13, and Glu and position B21) give a total negative charge of −4. Thus, the net charge on human insulin is 0.

Acylation of a Lys at position 29 of insulin removes a basic site thus lowering the net positive charge of the acylated material by one with respect to native human insulin. However, the presence of two basic amino acid groups such as Arg at positions 31 and 32 brings the net positive charge for a mono-acylated di-arginine species to plus one if the rest of the amino acids remain the same as in insulin. Similarly, mono-acylated tri-arginine species, with three additional Arg residues, will have a net positive charge of plus two. The results for species where the Pro at position 28 of the B-Chain and the Lys at position 29 of the B-Chain are switched give the same results. However, it will be readily recognized by one of skill in the art that when a neutral, basic, or acidic amino acid is substituted for another amino acid, the overall charge of the resulting species may change, but may still be calculated as having a net charge as compared to that of human insulin.

A "pharmaceutically-acceptable salt" of a fatty acid-acylated insulin analog means a salt formed between any one or more of the charged groups in the insulin analog and any one or more pharmaceutically-acceptable, non-toxic cations or anions. Organic and inorganic salts include, for example, those prepared from acids such as hydrochloric, sulfuric, sulfonic, tartaric, fumaric, hydrobromic, glycolic, citric, maleic, phosphoric, succinic, acetic, nitric, benzoic, ascorbic, p-toluenesulfonic, benzenesulfonic, naphthalenesulfonic, propionic, carbonic, and the like. Other pharmaceutically acceptable salts include, for example, ammonium, sodium, potassium, calcium, or magnesium salts of the fatty acid-acylated insulin analogs.

The term "complex" means a compound in which a transition metal is coordinated to at least one ligand. Ligands include nitrogen-containing molecules, such as insulins, peptides, amino acids, and TRIS, among many other compounds. The fatty acid-acylated insulin analogs used in the present invention may exist as complexes with divalent metal ions, preferably cobalt or zinc, and most preferably zinc, wherein protein molecules act as ligands of the metal ions.

A "pharmaceutically-acceptable complex" of an insulin analog means a complex formed between one or more groups in the insulin analog that may serve as an electron-donating ligand, and one or more pharmaceutically-acceptable, positively-charged metals. The transition metals, the alkaline metals, and the alkaline earth metals are examples of metals that are known to form complexes with insulin. Preferred metals that can be added to the formulations of the present invention include metals in the +2 oxidation state. The transition metals are preferred complexing agents and cobalt and zinc are preferred metals that can be added to the formulations. Zinc is a particularly preferred metal.

The term "preservative" refers to a compound added to a pharmaceutical formulation to act as an anti-microbial agent. A parenteral formulation must meet guidelines for preservative effectiveness to be a commercially viable multi-use product. Among preservatives known in the art as being effective and acceptable in parenteral formulations are benzalkonium chloride, benzethonium, chlorohexidine, phenol, m-cresol, benzyl alcohol, methylparaben, chlorobutanol, o-cresol, p-cresol, chlorocresol, resorcinol, phenylmercuric nitrate, thimerosal, benzoic acid, and various mixtures thereof. See, e.g. Wallhäusser, K-H., Develop. Biol. Standard. 24, pp. 9–28 (S. Krager, Basal 1974). Certain phenolic preservatives, such as phenol and m-cresol, are known to bind to insulin-like molecules and thereby to induce conformational changes that increase either physical or chemical stability, or both [Birnbaum, D. T., et al., *Pharmaceutical Res.*, 14, 25 (1997); Rahuel-Clermont, S., et al., *Biochemistry*, 36, 5837–5845 (1997)]. Preferred preservatives in formulations of the mono-acylated insulin analogs of the present invention include m-cresol, phenol, or mixtures thereof.

The term "buffer" or "pharmaceutically-acceptable buffer" refers to a compound that is known to be safe for use in insulin and insulin analog formulations and that has the effect of controlling the pH of the formulation at the pH desired for the formulation. Pharmaceutically-acceptable buffers for controlling pH at a moderately acidic pH include, but are not limited to such compounds as phosphate, acetate, citrate, TRIS, arginine, or histidine. TRIS is a commonly used buffer also known as tris(hydroxymethyl) aminomethane and tromethamine.

The term "isotonicity agent" refers to a compound that is tolerated physiologically and imparts a suitable tonicity to a formulation to prevent the net flow of water across the cell membrane. Compounds, such as, but not limited to, glycerin, are commonly used for such purposes at known concentrations. Glycerin is also known as glycerol. Other acceptable isotonicity agents include salts, e.g., NaCl, dextrose, mannitol, and lactose. Glycerin at a concentration of 12 to 25 mg/mL is preferred as an isotonicity agent. Glycerin at a concentration of 14 to 18 mg/mL is more preferred, and glycerin at a concentration of 16 mg/mL is most preferred in formulations of the present invention.

The mono-acylated insulin analogs of the present invention are suitable for treating conditions such as diabetes or hyperglycemia. In particular, the analogs of the invention are suitable for reducing blood glucose levels in people with diabetes or hyperglycemia. The effectiveness of the analogs of the invention in reducing blood glucose levels in patients in need of such treatment, and their time-action compared with insulin or monomeric insulin, can be determined by determined using the art-recognized techniques described elsewhere in this application.

As used herein, the term "hyperglycemia," which is well known in the art, describes a condition characterized by a blood glucose level that is higher than that found in a normal human. Normal human fasting blood glucose levels are less than 110 mg/dL. The Expert Committee on the Diagnosis and Classification of Diabetes Mellitus, *Diabetes Care*, 21 (Suppl. 1), S5–S19 (1992).

As used herein, the term "effective amount" refers to that amount of one or more insulin analogs of the present invention needed to lower or maintain blood glucose levels either therapeutically or prophylactically. This amount typically may range from about 10 units or more per day to about 60 units per day(or about 0.3 to about 2 mg assuming approximately 29 units per mg). However, it is to be understood that the amount of the insulin analog of the present invention actually administered will be determined by a physician in light of the relevant circumstances, including, the condition being treated (i.e. the cause of the hyperglycemia), the particular analog to be administered, the chosen parenteral route of administration, the age, weight, and response of the individual patient, and the severity of the patient's symptoms. Therefore, the above dosage ranges are not intended to limit the scope of the invention in any manner.

The acylated insulin analogs of the invention are administered to a patient in need thereof, such as a patient suffering from diabetes or hyperglycemia, by means of pharmaceutical compositions containing an effective amount of at least one insulin analog of the present invention in combination with one or more pharmaceutically acceptable excipients or carriers. For these purposes, the pharmaceutical compositions may typically be formulated so as to contain about 100 units per mL or similar concentrations containing an effective amount of the insulin analogs of the present invention. These compositions are typically, though not necessarily, parenteral in nature and may be prepared by any of a variety of techniques using conventional excipients or carriers for parenteral products which are well known in the art. [See, for example, Remington's Pharmaceutical Sciences, 17th Edition, Mack Publishing Company, Easton, Pa., USA (1985)].

Parenteral formulations of the present invention can be prepared using conventional dissolution and mixing procedures. To prepare a suitable formulation, for example, a measured amount of insulin analog in water is combined with the desired preservative in water in quantities sufficient to provide the protein and preservative at the desired concentration. The pH of the formulation may be adjusted to moderate acidity either before or after combining the insulin analog and the preservative. The formulation is generally sterile-filtered prior to administration.

The term "trypsin" refers to any of the mammalian serine proteases which catalyze the hydrolysis of the amide bond formed by the α-carboxyl group of a basic amino acid and the α-amino group of the adjacent amino acid.

An "enzyme having trypsin-like activity" includes trypsin from any source, derivatives of trypsin, such as TPCK-trypsin, and analogs of trypsin that retain trypsin activity.

The term "proinsulin-like precursor" means a single-chain peptide comprising, an insulin analog and a connecting bond or a connecting peptide, the connecting peptide having between 1 and about 37 amino acids, wherein the connecting bond or connecting peptide connects to a terminal amino acid of the A-chain and to a terminal amino acid of the B-chain by an α-amide bond or by two α-amide bonds, respectively, and wherein none of the amino acids in the connecting peptide is cysteine, and wherein the C-terminal amino acid of the connecting peptide is Lys or Arg. One example of a suitable connecting peptide is the C chain of human proinsulin. See U.S. Pat. No. 5,491,216 (Hoffman). A specific group of proinsulin-like precursors have the formula X-B-C-A or have the formula X-A-C-B, wherein:

X is hydrogen or is a peptide of from 1 to about 100 amino acids that has either Lys or Arg at its C-terminal amino acid;

A is an A-chain of SEQ ID NO:1;

C is a peptide of from 1 to about 35 amino acids, none of which is cysteine, wherein the C-terminal amino acid is Lys or Arg; and B is a B-chain of SEQ ID NO:2.

Disulfide bonds are also present in a proinsulin-like precursor. In particular, Cys at position 6 of the A-chain is joined with Cys at position 11 of the A-chain by a disulfide bond, Cys at position 7 of the B-chain is joined to Cys at position 7 of the A-chain by a disulfide bond, and Cys at position 19 of the B-chain is joined to 25 Cys at position 20 of the A-chain by a disulfide bond. Exposure of the proinsulin-like precursor having formula X-B-C-A or having formula X-A-C-B to an enzyme having trypsin-like activity results in the formation of certain insulin analogs of the present invention. Specifically, with reference to SEQ ID NO:2, insulin analogs wherein Xaa at position 28 of the B-chain is Pro, Asp, Leu, Val, or Ala, Xaa at position 29 of the B-chain is Pro or Lys, and Xaa at position 27 of the B-chain is absent are formed from X-B-C-A or X-A-C-B by treatment with trypsin.

The term "activated fatty acid ester" means a fatty acid which has been activated using general techniques described. Riordan, J. F. *Methods of Enzymology*, XXV, 494–499 (1972) and Lapidot et al., *J. of Lipid Res.*, 8, 142–145 (1967). Activated fatty acid ester includes derivatives of commonly employed acylating agents such as hydroxybenzotriazide (HOBT), N-hydroxysuccinimide and derivatives thereof. A preferred activated ester is N-succinimidyl palmitate.

The term "basic conditions" as used herein refers to the basicity of the reaction. To selectively acylate an insulin analog at the ε-amino group, the reaction must be carried out with substantially all the free amino groups deprotonated. In an aqueous solvent or co-solvent, basic conditions means the reaction is carried out at a pH greater than 9.0. In an organic solvent, the reaction is carried out in the presence of a base with basicity equivalent to a $pK_a$ greater than or equal to 10.75 in water.

Preparation of Insulin Analogs

The mono-acylated insulin analogs of the present invention are prepared by first synthesizing the insulin analog portion of the molecule, and then acylating the insulin analog.

The insulin analogs of the present invention are synthesized by well-known chemical methods alone, by recombinant DNA methods alone, or by a combination of chemical and recombinant DNA methods. The following list briefly outlines several basic ways to synthesize these insulin analogs. The list is not exhaustive, and other variations of the basic schemes are possible, and would be known to the skilled artisan.

1) Synthesis of a human insulin A-chain analog (SEQ ID NO:1) by standard biosynthetic methods using recombinant DNA and separate synthesis of a human insulin B-chain or a human insulin B-chain analog (SEQ ID NO:2) by standard biosynthetic methods using recombinant DNA, followed by combination of the chains via known disulfide chemistry, as disclosed in Chance, et al., U.S. Pat. No. 4,421,685, issued Dec. 20, 1983.

2) Synthesis of a human insulin A-chain analog (SEQ ID NO:1) by standard chemical synthesis methods and separate synthesis of a human insulin B-chain or a human insulin B-chain analog (SEQ ID NO:2) by standard chemical synthesis methods, followed by their combination via known disulfide chemistry, as referred to above.

3) Chemical synthesis of one of the chains and biosynthesis from recombinant DNA of the other, followed by their combination via known disulfide chemistry, as referred to above.

4) Cleavage of a proinsulin-like precursor, which is made by chemical synthesis, or, preferably, by biosynthesis starting from recombinant DNA, using an enzyme having trypsin-like activity.

Chemical Synthesis

The principles of solid phase chemical synthesis of polypeptides are well-known and may be found in general texts in the area. [See, e.g., H. Dugas and C. Penney, Bioorganic Chemistry, (1981) Springer-Verlag, N.Y., pp. 54–92.] Peptides of the present invention may be synthesized by solid-phase methodology utilizing an Applied Biosystems 430A peptide synthesizer (commercially available from Applied Biosystems, Foster City, Calif.) and synthesis cycles supplied by Applied Biosystems. Protected amino acids, such as t-butoxycarbonyl-protected amino acids, and other reagents are commercially available from many chemical supply houses.

Sequential t-butoxycarbonyl chemistry using double couple protocols are applied to the starting p-methyl benzhydryl amine resins for the production of C-terminal carboxamides. For the production of C-terminal acids, the corresponding pyridine-2-aldoxime methiodide resin is used. Asparagine, glutamine, and arginine are coupled using preformed hydroxy-benzotriazole esters. The following side chain protection groups may be used:

Arg, Tosyl
Asp, cyclohexyl
Glu, cyclohexyl
Ser, Benzyl
Thr, Benzyl
Tyr, 4-bromo carbobenzoxy.

Removal of the t-butoxycarbonyl moiety (deprotection) may be accomplished with trifluoroacetic acid (TFA) in methylene chloride. Following completion of the synthesis, the peptides may be deprotected and cleaved from the resin with anhydrous hydrogen fluoride containing 10% meta-cresol. Cleavage of the side chain protecting group(s) and of the peptide from the resin is carried out at zero degrees centigrade or below, preferably −20° C. for thirty minutes followed by thirty minutes at 0° C.

After removal of the hydrogen fluoride, the peptide/resin is washed with ether, and the peptide extracted with glacial acetic acid and then lyophilized. Purification is accomplished by size-exclusion chromatography, such as, on a Sephadex G-10 (Pharmacia) column in 10% acetic acid.

Synthesis using Recombinant DNA Technology

The individual A- and B-chains of the present invention or a proinsulin-like precursor of the insulin analogs of the present invention may be biosynthesized starting from recombinant DNA. Recombinant methods are preferred if a high yield is desired. A general method for the construction of any desired DNA sequence is provided in J. Brown, et al., *Methods in Enzymology*, 68, 109 (1979). [See also, J. Sambrook, et al., Molecular Cloning: A Laboratory Manual, Cold Spring Harbor, N.Y. (1989)].

The basic steps in the recombinant production of desired proteins are:

a) constructing a synthetic or semi-synthetic DNA encoding the protein of interest;

b) integrating said DNA into an expression vector in a manner suitable for the expression of the protein of interest, either alone or as a fusion protein;

c) transforming an appropriate eukaryotic or prokaryotic host cell with said expression vector, d) culturing said transformed or transfected host cell in a manner to express the protein of interest; and e) recovering and purifying the recombinantly produced protein of interest.

In general, prokaryotes are used for cloning of DNA sequences in constructing the vectors of this invention. Prokaryotes may also be employed in the production of the protein of interest. For example, the *Escherichia coli* K12 strain 294 (ATCC No. 31446) is particularly useful for the prokaryotic expression of foreign proteins. Other strains of *E. coli* which may be used (and their relevant genotypes) include those shown in Table 1.

TABLE 1

| Genotypes of *E. coli* that may be used to synthesize insulin analogs. | |
|---|---|
| Strain | Genotype |
| DH5α | F⁻ (φ80dlacZΔM15), Δ(lacZYA-argF)U169 supE44, λ⁻, hsdR17($r_K^-$, $m_K^+$), recA1, endA1, gyrA96, thi-1, relA1 |
| HB101 | SupE44, hsdS20($r_B^- m_B^-$), recA13, ara-14, proA₂ lacY1, galK2, rpsL20, xyl-5, mtl-1, mcrB, mrr |
| JM109 | RecA1, e14⁻(mcrA), supE44, endA1, hsdR17($r_K^-$, $m_K^+$), gyrA96, relA1, thi-1, (lac-proAB), |

TABLE 1-continued

Genotypes of *E. coli* that may be used to synthesize insulin analogs.

| Strain | Genotype |
| --- | --- |
| RR1 | F'[traD36, proAB + lacI$^q$, lacZ M 15] SupE44, hsdS20(r$_B^-$m$_B^-$), ara-14 proA$_2$, lacY1, galK2, rpsL20, xyl-5, mtl-5 |
| χ1776 | F$^-$, ton, A53, dapD8, minA1, supE42 (glnV42), Δ(gal-uvrB)40, minB2, rfb-2, gyrA$_2$5, thyA142, oms-2, metC65, oms-1, Δ(bioH-asd)29, cycB2, cycA1, hsdR2, λ$^-$ |
| 294 | EndA, thi$^-$, hsr$^-$, hsm$_K^+$ (U.S. Pat. No. 4,366,246) |
| LE392 | F$^-$, hsdR514 (r$^-$m$^-$), supE44, supF58, lacY1, or Δlac(I-Y)6, galK2, glaT22, metB1, trpR55, λ$^-$ |

These strains are all commercially available from suppliers such as: Bethesda Research Laboratories, Gaithersburg, Md. 20877 and Stratagene Cloning Systems, La Jolla, Calif. 92037; or are readily available to the public from sources such as the American Type Culture Collection, 12301 Parklawn Drive, Rockville, Md. 10852-1776.

Except where otherwise noted, these bacterial strains can be used interchangeably. The genotypes listed are illustrative of many of the desired characteristics for choosing a bacterial host and are not meant to limit the invention in any way. The genotype designations are in accordance with standard nomenclature. [See, for example, J. Sambrook, et al., supra.] A preferred strain of *E. coli* employed in the cloning and expression of the genes of this invention is RV308, which is vailable from the ATCC under accession number ATCC 31608, and is described in U.S. Pat. No. 4,551,433, issued Nov. 5, 1985.

In addition to the strains of *E. coli* discussed supra, bacilli such as *Bacillus subtilis*, other enterobacteriaceae such as *Salmonella typhimurium* or *Serratia marcescans*, and various Pseudomonas species may be used. In addition to these gram-negative bacteria, other bacteria, especially Streptomyces, spp., may be employed in the prokaryotic cloning and expression of the proteins of this invention.

Promoters suitable for use with prokaryotic hosts include the β-lactamase [vector pGX2907 (ATCC 39344) contains the replicon and β-lactamase gene] and lactose promoter systems [Chang, et al., *Nature* (London), 275, 615 (1978); and Goeddel, et al., *Nature* (London), 281, 544 (1979)], alkaline phosphatase, the tryptophan (trp) promoter system [vector pATH 1 (ATCC 37695) is designed to facilitate expression of an open reading frame as a trpE fusion protein under control of the trp promoter] and hybrid promoters such as the tac promoter (isolatable from plasmid pDR540 ATCC-37282). However, other functional bacterial promoters, whose nucleotide sequences are generally known, enable one of skill in the art to ligate them to DNA encoding the proteins of the instant invention using linkers or adapters to supply any required restriction sites. Promoters for use in bacterial systems also will contain a Shine-Dalgarno sequence operably linked to the DNA encoding the desired polypeptides. These examples are illustrative rather than limiting.

The proteins of this invention may be synthesized either by direct expression or as a fusion protein comprising the protein of interest as a translational fusion with another protein or peptide which may be removable by enzymatic or chemical cleavage. It is often observed in the production of certain peptides in recombinant systems that expression as a fusion protein prolongs the lifespan, increases the yield of the desired peptide, or provides a convenient means of purifying the protein of interest. A variety of peptidases (e.g., trypsin) which cleave a polypeptide at specific sites or digest the peptides from the amino or carboxy termini (e.g. dipeptidylaminopeptidase) of the peptide chain are known. Furthermore, particular chemicals (e.g. cyanogen bromide) will cleave a polypeptide chain at specific sites. The skilled artisan will appreciate the modifications necessary to the amino acid sequence (and synthetic or semi-synthetic coding sequence if recombinant means are employed) to incorporate site-specific internal cleavage sites. [See, e.g., P. Carter, "Site Specific Proteolysis of Fusion Proteins", Chapter 13 in Protein Purification: From Molecular Mechanism to Large Scale Processors, American Chemical Society, Washington, D.C. (1990)].

As summarized above, certain of the insulin analogs of the present invention are made by treating a proinsulin-like precursor having the formula X-B-C-A or having the formula X-A-C-B with an enzyme having trypsin-like activity [See, Belagaje, R. M. et al., U.S. Pat. No. 5,304,473, issued Apr. 19, 1994, for an A-C-B proinsulin. The precursor is preferably biosynthesized in an organism transformed with the appropriate recombinant DNA structures. The expressed peptide is purified, the three disulfide bonds of the precursor are properly formed, and the precursor is treated with an enzyme having trypsin-like activity to cleave X and to excise C. The use of enzymes having trypsin-like activity to cleave proinsulin-like precursors is well-known [Chance, R. E., et al., *Science*, 161, 165–167 (1968); Kemmler W., et al., *J. Biol. Chem.*, 246, 6786–6791 (1971); Frank, B. H. et al., in Peptides: Synthesis, Structure, Function, Proceedings of the Seventh American Peptide Symposium, Ed., Rich, D. H. and Gross, E., Pierce Chemical Company (1981) pp 729–38; Hansen, H. et al., U.S. Pat. No. 5,149,777, issued Sep. 22, 1992; Balschmidt, et al., U.S. Pat. No. 5,164,366, issued Nov. 17, 1992. Methods for properly forming the three disulfide bonds of a proinsulin-like precursor are also well-known [See, e.g., Frank, B. H. U.S. Pat. No. 4,430,266, issued Feb. 7, 1984.

Acylation

The acylation of free amino groups of proteins, including insulin, is known in the art. General methods of acylation are set forth by Riordan, J. F. and Vallee, B. L., *Methods of Enzymology*, XXV, 494–499 (1972) and include the use of activated esters, acid halides, or acid anhydrides. The use of activated esters, in particular N-hydroxysuccinimide esters, of fatty acids is a particularly advantageous means of acylating a free amino acid with a fatty acid. Lapidot, Y. et al., *J. of Lipid Res*. 8, 142–145 (1967). Lapidot et al. describe the preparation of N-hydroxysuccinimide esters and their use in the preparation of N-lauroyl-glycine, N-lauroyl-L-serine, and N-lauroyl-L-glutamic acid.

To selectively acylate the ε-amino group, various protecting groups may be used to block the α-amino group during the coupling. The selection of a suitable protecting group is known to one skilled in the art and includes p-methoxybenzoxy-carbonyl (pmZ). Preferably, the ε-amino group is acylated in a one step synthesis without the use of amino-protecting groups. The acylation is carried out by reacting the activated fatty acid ester with the ε-amino group of the protein under basic conditions in a polar solvent. The basicity of the reaction must be sufficient to deprotonate all the free amino groups of the insulin analog. Under weakly basic conditions, all the free amino groups are not deprotonated and preferential acylation of the N-terminal or α-amino groups results. In an aqueous solvent or co-solvent, basic conditions means the reaction is carried out at a pH greater than 9.0. Because protein degradation results at a pH range exceeding 12.0, the pH of the reaction mixture is preferably 10.0 to 11.5, and most preferably 10.5. The pH measurement of the reaction of the reaction mixture in a mixed organic and aqueous solvent is the pH of the aqueous solvent prior to mixing.

In a non-aqueous solvent, the selective acylation of the ε-amino group is carried out in the presence of a base with basicity equivalent to a $pK_a$ greater than or equal to 10.75 in water in order to sufficiently deprotonate the ε-amino group (s). That is, the base must be at least as strong as triethylamine. Preferably, the base is tetramethylguanidine, diisopropylethylamine, or tetrabutylammonium hydroxide. The use of a weaker base results in the acylation of the α-amino groups.

The choice of solvent is not critical and dependent largely on the solubility of the insulin analog and the fatty acid ester. The solvent may be wholly organic. Generally acceptable organic solvents include DMSO, DMF and the like. Aqueous solvent and mixtures of aqueous and organic solvents are also operable. The selection of the polar solvents is limited only by the solubility of the reagents. Preferred solvents are DMSO; DMF; acetonitrile and water; acetone and water; ethanol and water; isopropyl alcohol and water; isopropyl alcohol, ethanol, and water; and ethanol, propanol and water. Preferably, the solvent is acetonitrile and water; most preferably 50% acetonitrile. One skilled in the art would recognize that other polar solvents are also operable.

Generally, it is preferred that the activated fatty acid ester be in molar excess. Preferably the reaction is carried out with 1 to 4 molar equivalents, most preferably 1 to 2 molar equivalents, of the ester. One skilled in the art would recognize that at very high levels of activated ester, bis- or tri-acylated product will be produced in significant quantity.

The temperature of the reaction is not critical. The reaction is carried out at between 20 to 40 degrees Celsius and is generally complete in 15 minutes to 24 hours.

After acylation, the product is purified by standard methods such as reverse phase hydrophobic chromatography. Thereafter, the product is recovered by standard methods such freeze drying or by crystallization.

Preparation and Use of Inventive Formulations

Formulations of the present insulin analogs for parenteral administration may be prepared by suspending or dissolving the desired amount of a monoacylated di-arginine or tri-arginine insulin analog of the present invention in a non-toxic liquid vehicle suitable for injection, such as an aqueous medium, and sterilizing the suspension or solution. Alternatively, a measured amount of the compound may be placed in a vial, and the vial and its contents sterilized and sealed. An accompanying vial or vehicle can be provided for purposes of dissolving the compound prior to administration.

Pharmaceutical compositions adapted for parenteral administration typically employ diluents, excipients and carriers such as water and water-miscible organic solvents such as glycerin, aqueous propylene glycol, N,N-dimethylformamide and the like. Examples of such pharmaceutical compositions include sterile, isotonic, aqueous saline solutions of the acylated di-arginine or tri-arginine insulin analogs that can be buffered with a pharmaceutically acceptable buffer and that are pyrogen free. Additionally, the parenteral pharmaceutical formulation may contain preservatives such as meta-cresol or phenol, or compounds added to adjust the pH of the final product, such as, sodium hydroxide or hydrochloric acid.

Variations in these formulations would be recognized by one of ordinary skill in the art. For example, the manner in which components are added, the manner in which pH is adjusted, the surfactant used, if any, the isotonicity agent, the type and amount of salt-forming or complex-forming agent, the temperature and ionic strength at which the formulation is prepared, may be optimized for the concentration and means of administration used.

In one embodiment, preferred formulations of the present invention comprise a monoacylated di-arginine or tri-arginine insulin analog, at a pH value between about 3.0 and about 3.8. Most preferably, the pH of such formulations is about 3.5. The skilled artisan will recognize that in formulations at these pH values, the majority of the inventive insulin analog will be soluble. With respect to the pH of these formulations, "about" means plus or minus 0.05 pH units. "About 3.8" means 3.75 to 3.85. Such formulations may include various compounds well known in the art, such as a preservative.

Thus, the invention encompasses a method of treating diabetes, comprising administering to a patient in need of such treatment, a formulation comprising a monoacylated di-arginine or tri-arginine insulin analog of the present invention, wherein the pH of the formulation is between about pH 3.0 and about 3.8. Such a method can also be practiced using such a formulation, with a pH value of about 3.5.

In another embodiment, preferred formulations of the present invention comprise a monoacylated di-arginine or tri-arginine insulin analog, having a pH of between about 4.5 and about 7.6. Another preferred pH range is about 5.0 and about 7.0. Most preferably, the pH of such formulations is about 6.5. The skilled artisan will recognize that in these formulations, the majority of the inventive insulin analog will be insoluble. With respect to the pH of these formulations, "about" means plus or minus 0.05 pH units. Such formulations may include various compounds well known in the art, such as a preservative.

Thus, the invention encompasses a method of treating diabetes, comprising administering to a patient in need of such treatment, a formulation comprising a monoacylated di-arginine or tri-arginine insulin analog of the present invention, wherein the pH of the formulation is between about pH 4.5 and about 7.6. Such a method can also be practiced using such a formulation, with a pH value of between about 5.0 and about 7.0. Such a method can also be practiced using such a formulation, with a pH value of between about 6.5.

In yet other embodiments of the invention, preferred formulations of the present invention comprise a monoacylated di-arginine or tri-arginine insulin analog, wherein at least about 50% or about 60% or about 70% or about 80% or about 90% or about 95% or about 96% or about 97% of the analog is insoluble. With respect to solubility percentages, "about" means plus or minus 2% of the given value. For example, "about 50%" means 48 to 52%. Formulations having at least about 50% are particularly preferred.

Thus, the invention encompasses a method of treating diabetes, comprising administering to a patient in need of such treatment, a formulation comprising a monoacylated di-arginine or tri-arginine insulin analog of the present invention, wherein at least about about 50% or about 60% or about 70% or about 80% or about 90% or about 95% or about 96% or about 97% of the analog is insoluble.

The skilled artisan will recognize that there are many suitable methods for determining whether a given compound, such as a monoacylated di-arginine or tri-arginine insulin analog, is soluble. Such methods involve first determining the protein concentration of the formulation comprising the insulin analog. Methods for determining protein concentration are well known in the art, and include optical density, radioimmunoassay, fluorescence, capillary electrophoresis, SDS polyacrylamide gel electrophoresis, and HPLC. Second, the insoluble material is separated from the soluble material using a technique to physically separate the soluble and insoluble analog, such as centrifugation. Following centrifugation, the protein concentration of the supernatent of the centrifuged material is determined using one of the many techniques that are well known in the art.

The following examples are provided merely to further illustrate the invention. The scope of the invention should not be construed as merely consisting of the following examples.

PREPARATION 1

$Gly^{A21}Arg^{B31}Arg^{B32}$ and
$Arg^{A0}Gly^{A21}Arg^{B31}Arg^{B32}$-Human Insulin Analogs $Gly^{A21}Arg^{B31}Arg^{B32}$ and $Arg^{A0}Gly^{A21}Arg^{B31}Arg^{B32}$ human insulin analogs were obtained from an $E.\ coli$ fermentation in which a $Gly^{A21}$-human proinsulin precursor molecule was overexpressed into inclusion bodies. Polynucleotides encoding these precursor molecules were prepared using standard recombinant DNA techniques, as discussed above.

A portion (94.7 g) of inclusion bodies was solubilized in 500 mL of 6 M guanidine-HCl containing 0.1 M TRIS, 0.27 M sodium sulfite, and 0.1 M sodium tetrathionate, pH 10.5 at room temperature. The pH was raised from 7.7 to 10.4 with 5 N NaOH while stirring vigorously. The pH was quickly lowered to 8.8 with 12 N HCl. After vigorously stirring in an open container for 45 minutes, the pH was lowered to 2.1 with H3PO4 and the sample centrifuged overnight at 4° C. The supernatant was decanted and stored at 4° C. for additional processing. The pellet was re-extracted with 200 mL of additional pH 10.5 solution (see above) and then centrifuged for 3 hours at 4° C. This and the previously obtained supernatant were each diluted 4x with 100 mM NaH2PO4, pH 4, precipitating the product and other acidic components. After allowing the precipitate to settle, most of the supernatant was decanted and discarded.

The resulting suspension was centrifuged, followed by decanting and discarding of additional supernatant, leaving wet pellets of the crude $Gly^{A21}$-human proinsulin S-sulfonate precursor. The pellets were solubilized in 1.5 liters of 7 M deionized urea, adjusting the pH to 8 with 5 N NaOH and stirring over several hours at 4° C. Salt (NaCl) was then added to achieve 1 M concentration and the sample was loaded onto a 14x20 cm XAD-7 (Toso-Haas, Montgomeryville, Pa.) column, previously flushed with 50% acetonitrile/50% 50 mM ammonium bicarbonate, 10% acetonitrile/90% 50 mM ammonium bicarbonate, and finally with 7 M deionized urea/1M NaCl/20 mM TRIS, pH 8. Once loaded, the column was pumped with 4.5 liters of a 7 M deionized urea/1 M NaCl/20 mM TRIS, pH 8 solution, followed by 3 liters of 50 mM ammonium bicarbonate/1 M NaCl, and 6 liters of 50 mM ammonium bicarbonate. The column was eluted with a linear gradient of acetonitrile in 50 mM ammonium bicarbonate, while monitoring the eluant by UV at 280 nm.

The peak of interest, partially purified $Gly^{A21}$-human proinsulin S-sulfonate precursor, was collected, lyophilized, and subjected to a folding/disulfide bond procedure as follows. A quantity (5.4 g) of the precursor was dissolved in 3 liters of 20 mM glycine, pH 10.5, 4° C. Then, 15 mL of 240 mM cysteine HCl were added with stirring, while maintaining the pH at 10.5 and the temperature at 4° C. The reaction solution was stirred gently at 4° C. for 27 hours and then quenched by lowering the pH to 3.1 with H3PO4. Acetonitrile (155 mL) was added, and the solution was then loaded onto a 5x25 cm C4 reversed-phase column (Vydac, Hesperia Calif.) previously pumped with 60% acetonitrile/39.9% H2O/0.1% TFA and equilibrated in 10% acetonitrile/90% H2O/0.1% TFA. Once loaded, the column was pumped with 1 liter of 10% acetonitrile/89.9% 1H2O/0.1% TFA, then eluted with a linear gradient of acetonitrile in 0.1% TFA while monitoring at 280 nm. Selected fractions were pooled and lyophilized with a recovery of 714 mg.

One of ordinary skill in the art will recognize that the $Gly^{A21}$ human proinsulin precursor can be cleaved to obtain either $Gly^{A21}Arg^{B31}Arg^{B32}$ or $Arg^{A0}Gly^{A21}Arg^{B31}Arg^{B32}$ human insulin analogs. The preparation of the di-arginine species and tri-arginine species is described below.

For conversion of the proinsulin precursor to the desired insulin analog, 697 mg of the $Gly^{A21}$-human proinsulin precursor was dissolved in 70 mL 50 mM ammonium bicarbonate, then chilled to 4° C., pH 8.3. A volume (0.14 mL) of a 1 mg/mL solution of pork trypsin (Sigma Chemical Company, St. Louis, Mo.) in 0.01 N HCl was added to the sample solution which was stirred gently at 4° C. for about 24 hours. An additional 0.14 mL of the trypsin solution was added to the reaction solution which was then stirred for an additional 21 hours, 45 minutes. The reaction was quenched by lowering the pH to 3.2 with 0.7 mL glacial acetic acid and 0.3 mL H3PO4.

The quenched solution containing the tryptic cleavage reaction was diluted 4x with 30% acetonitrile/70% 50 mM acetic acid, pH 3.1, and loaded onto a 1 x30 cm S HyperD F (Biosepra, Marlborough, Mass.) column (23.5 mL) previously pumped with 30% acetonitrile/70% 50 mM acetic acid/500 mM NaCl, pH 3.3, and equilibrated in 30% acetonitrile/70% 50 mM acetic acid. Once loaded, the column was pumped with about 50 mL of 30% acetonitrile/70% 50 mM acetic acid, then the tryptic cleavage products were eluted with a linear gradient of NaCl in 30% acetonitrile/50 mM acetic acid while monitoring the eluant at 276 nm.

The above-described procedure will produce both the di-arginine analog ($Arg^{A0}Gly^{A21}Arg^{B31}Arg^{B32}$),and the tri-arginine analog ($Arg^{A0}Gly^{A21}Arg^{B31}Arg^{B32}$ human insulin), although the di-arginine analog will be produced in relatively higher amounts. Shorter reaction times and lower quantities of trypsin will favor the production of a higher proportion of the tri-arginine species. In addition to the procedure described bove, other techniques for producing di- and tri-arginine species are well known in the art. See, for example, U.S. Pat. No. 5,491,216 (Hoffmann, J. A., et al.) and Zeuzem, S., et al. $Diabetologia$ 33:65–71 (1990).

The fractions containing di-arginine and tri-arginine species eluted from the 1x30 cm S HyperD F (Biosepra) column were identified using analytical HPLC. Other techniques are suitable for determining the identity of peaks eluted from a purification column. For example, capillary electrophoresis carried out at a low pH, such as pH 4, will distinguish between the di-arginine and tri-arginine species, because the tri-arginine species contains one more positive charge than the di-arginine species. Another technique that can be used to identify the eluted material is N-terminal amino acid sequence analysis. The tri-arginine species will have an arginine at the N-terminus of the A chain, whereas the di-arginine species will have a glycine at its N-terminus. Mass spectroscopy also can be used to detect di- and tr-arginine species.

Selected fractions containing the $Gly^{A21}Arg^{B31}Arg^{B32}$-human insulin analog were pooled based on analytical HPLC assays, diluted 3× with purified water, and loaded onto a 2.2×25 cm C4 reversed-phase column (Vydac, Hesperia Calif.), previously pumped with 60% acetonitrile/ 39.9% H2O/0.1% TFA, then 10% acetonitrile/89.9% H2O/ 0.1% TFA. Once loaded, the column was pumped with about 200 mL of 10% acetonitrile/89.9% H2O/0.1% TFA, then eluted with a linear gradient of acetonitrile in 0. 1% TFA. Selected fractions were pooled and lyophilized giving a recovery of 101 mg. Analytical HPLC revealed a purity of greater than 95% of the main peak. Electrospray mass spectroscopy (ES/MS) analysis of the purified protein yielded a molecular weight of 6062.9. This value is nearly identical to the theoretical molecular weight of 6063.0.

Thus, to isolate the tri-arginine analog, those fractions that contained the $Arg^{A0}Gly^{A21}Arg^{B31}Arg^{B32}$human insulin analog, from the S HyperD F (Biosepra) colurnn chromatography following trypsin cleavage, were combined. These fractions were then diluted 2× with purified water and loaded onto a 2.2×25 cm C4 (Vydac, Hesperia, Calif.) reversed-phase column. Once loaded, the column was pumped with 2 column volumes (c.v.) 10% acetonitrile/90% 0.1% TFA, and then it was eluted with a linear gradient of acetonitrile in 0.1% TFA. Selected fractions were combined, frozen and lyophilized. 32 mg of lyophilized $Arg^{A0}Gly^{A21}Arg^{B31}Arg^{B32}$human insulin analog were recovered. Analytical HPLC indicated a purity of greater than 82% main peak. Electrospray mass spectroscopy (ES/ MS) analysis of the purified protein yielded a molecular weight of 6218.9 (calculated theoretical molecular weight: 6219.2).

PREPARATION 2

Preparation of B29-N$^\epsilon$-Gly$^{A21}$Arg$^{B31}$Arg$^{B32}$-
Myristoyl and B29-N$^\epsilon$-Arg$^{A0}$Gly$^{A21}$Arg$^{B31}$Arg$^{B32}$-
Myristoyl Human Insulin Analogs The following describes the procedure utilized for acylating di-arginine and tri-arginine insulin analogs. The outline is to be read in conjunction with the data in Table 2 and the acylation procedure described above.

A measured mass of purified insulin analog was dissolved by adding to it a measured volume of 50 mM boric acid at pH 2.57. A measured volume of acetonitrile, equal to the volume of boric acid solution, was then added slowly with stirring. The "solvent" volume is the sum of the volumes of the boric acid and acetonitrile. The pH of the solution was then adjusted to between 10.2 and 10.5 by adding NaOH. In a separate container, a measured mass of an N-acyl-succinimide ("NAS") was dissolved in a measured volume of acetonitrile. A measured volume of the second solution was then added to the first solution. The reaction was then stirred at room temperature while maintaining the pH above 10.2, and the progress of the reaction was monitored by analyzing samples of the reaction mixture using HPLC. When HPLC indicated that the reaction was complete, the reaction was quenched by acidifying to pH 2–3. The reaction mixture was then subjected to purification using reverse-phase chromatography. A Pharmacia FPLC Chromatography System (Vydac C4 column (1×25 cm) configured for gradient elution, was connected to a UV detector and connected to a data recording device, such as a chart recorder or computer, and a fraction collector. The column was cleaned with buffer B (0.1% TFA, 70% ACN, pH 2) and then equilibrated with buffer A (0.1% TFA, 10% ACN). A diluted sample was added directly to the equilibrated column via the A pump of the FPLC. The column was then equilibrated to 100% buffer A, and the sample was eluted using a gradient of acetonitrile. The gradient system used to elute the sample was: (1) 0 minutes: 0% buffer B; (2) 30 minutes: 30% buffer B; (3) 210 minutes: 60% buffer B; (4) 270 minutes: 100% buffer B.

Table 2 provides experimental data, according to the outline above, for the synthesis of the derivatized proteins that were used to prepare various embodiments of the present invention. The molecular weight of the purified derivatives was confirmed using electrospray mass spectroscopy (ES/MS). Assignment of the acylation site was confirmed using chromatographic analysis (analytical HPLC). N-terminal amino acid analysis also can be used. The analytical HPLC was performed with an Altex Model 420 System Controller, two Beckman 11A pumps, a Bio-Rad Model AS-100 autosampler, a column heater, a UV detector connected to a data recording device, such as a chart recorder or computer. A Vydac C4 column (0.46×25 cm) was equilibrated with buffer A (0.1% TFA, 10% ACN), 20 µl of sample was applied, and sample eluted with the following gradient, using buffer B (0.1% TFA, 70% CAN): (1) 0 minutes: 0% buffer B; (2) 5 minutes: 0% buffer B; (3) 6 minutes: 30% buffer B; (4) 36 minutes: 60% buffer B; (5) 37 minutes: 100% buffer B; (6) 42 minutes: 100% buffer B; (7) 43 minutes: 0% buffer B; (8) 53 minutes: 0% buffer B. Elution of samples was detected by absorbance at 214 nm; flow rate was 1.0 ml/minute; temperature was 45° C. The same procedure was also used with a Jupiter C18 column (0.46×15 cm). When a series of samples was analyzed, injections were done every 54 minutes.

TABLE 2

Summary of acylation of various di-arginine and tri-arginine human insulin analogs.

| Starting protein | Gly$^{A21}$Arg$^{B31}$Arg$^{B32}$ human insulin analog | Arg$^{A0}$Gly$^{A21}$Arg$^{B31}$Arg$^{B32}$ Human insulin analog |
| --- | --- | --- |
| Protein mass (mg) | 43.3 | 45.6 |
| Solvent (mL) | 10 | 20 |
| NAS acyl chain | n-myristoyl | n-myristoyl |
| Mass of N-acyl-succinimide (mg) | 7.0 | 14.5 |
| Volume of acetonitrile to dissolve NAS (mL) | 1.0 | 1.0 |
| Volume of NAS solution added (mL) | .498 | 0.247 |
| Reaction time (min) | 43 | 36 |
| Total yield (%) | 43 | 52 |
| Mol. Wt. (theory) | 6273.38 | 6429.57 |
| Mol. Wt. (ES/MS) | 6273.5 | 6429.6 |
| HPLC Purity (%) | >99 | 98 |
| Acylation site (HPLC) | $\epsilon$-amino group of Lys at position B29 | $\epsilon$-amino group of Lys at position B29 |

PRERPARATION 3

Preparation of B29-N$^\epsilon$-Gly$^{A21}$Arg$^{B31}$Arg$^{B32}$-
Dodecanoyl and B29-N$^\epsilon$-Gly$^{A21}$Arg$^{B31}$Arg$^{B32}$-
Decanoyl Human Insulin Analogs The following is an outline of the synthesis of additional derivatized proteins. The outline is to be read together with the data in Table 3, below, to provide full synthetic schemes.

A 20 ml sample of purified Gly$^{A21}$Arg$^{B31}$Arg$^{B32}$-human insulin, pooled from a cation exchange column (S HyperD F (Biosepra)) and containing 1.7 mg/ml peptide (UV estimate), 0.4 M NaCl, and 30% acetonitrile (v/v), was made 50% acetonitrile with an additional 8 ml of acetonitrile, final volume is 28 ml and the pH was 3.6. This 28 ml solution of Gly$^{A21}$Arg$^{B31}$Arg$^{B32}$-human insulin was then split into two 14 ml portions. The pH of each solution was adjusted to between 10.6 and 10.9 using NaOH. In separate containers, a measured mass of C10 or C12-succinimide was dissolved in 0.5 ml of DMSO. Either C10 or C12-succinimide were added to the individual Gly(A21)di-Arg-human insulin solutions. The reaction was carried out at room temperature, the pH maintained above 10.2, and the progress of the reaction was monitored by analyzing samples of the reaction mixture using HPLC. After HPLC indicated reaction completion, the reaction was quenched by acidifying to pH 2–3.

The reaction mixture was then subjected to purification using a reversed-phase chromatography system. For the C12-B29-Gly$^{A21}$-di-arginine human insulin, the following system was used: A Pharmacia FPLC Chromatography System (Vydac C4 column (1×25 cm) configured for gradient elution, was connected to a UV detector and connected to a data recording device, such as a chart recorder or computer, and a fraction collector. The column was cleaned with buffer B (0.1% TFA, 70% ACN, pH 2) and then equilibrated with buffer A (0.1% TFA, 10% ACN). A diluted sample was added directly to the equilibrated column via the A pump of the FPLC. The column was then equilibrated to 100% buffer A, and the sample was eluted using a gradient of acetonitrile. The gradient system used to elute the sample was: (1) 0 minutes: 0% buffer B; (2) 20 minutes: 30% buffer B; (3) 180 minutes: 60% buffer B.

For the C10-B29-Gly$^{A21}$-di-arginine human insulin, the following system was used: A Pharmacia FPLC Chromatography System (Vydac C18 column (1×25 cm) configured for gradient elution, was connected to a UV detector and connected to a data recording device, such as a chart recorder or computer, and a fraction collector. The column was cleaned with buffer B (0.1% TFA, 70% ACN, pH 2) and then equilibrated with buffer A (0.1% TFA, 10% ACN). A diluted sample was added directly to the equilibrated column via the A pump of the FPLC. The column was then equilibrated to 100% buffer A, and the sample was eluted using a gradient of acetonitrile. The gradient system used to elute the sample was: (1) 0 minutes: 0% buffer B; (2) 20 minutes: 30% buffer B; (3) 180 minutes: 60% buffer B.

Table 3 provides experimental data, according to the outline above, for the synthesis of the derivatized proteins that were used to prepare various embodiments of the present invention. Molecular weight of the purified derivatives was confirmed by mass spectrometry via electrospray mass analysis (ES/MS). Assignment of the acylation site was based on a chromatographic analysis ("HPLC").

TABLE 3

Summary of acylation procedure for di-arginine human insulin analog.

| Starting protein | Gly$^{A21}$Arg$^{B31}$Arg$^{B32}$ human insulin analog | Gly$^{A21}$Arg$^{B31}$Arg$^{B32}$ human insulin analog |
|---|---|---|
| Protein mass (mg) | 17 | 17 |
| Solvent (mL) | 14 | 14 |
| NAS acyl chain | n-dodecanoyl | n-decanoyl |
| Mass of N-acyl-succinimide (mg) | 19.3 | 33.8 |

TABLE 3-continued

Summary of acylation procedure for di-arginine human insulin analog.

| Starting protein | Gly$^{A21}$Arg$^{B31}$Arg$^{B32}$ human insulin analog | Gly$^{A21}$Arg$^{B31}$Arg$^{B32}$ human insulin analog |
|---|---|---|
| Volume of DMSO (mL) | 0.5 | 0.5 |
| Fold excess N-acyl-succinimide used | 3 | 3 |
| Volume of NAS solution added (mL) | 0.0648 | 0.0335 |
| Reaction time (min) | 43 | 40 |
| Total yield (%) | 56.4* | 70.2* |
| Mol. Wt. (theory) | 6245.33 | 6217.27 |
| Mol. Wt. (ESMS) | 6245.3 | 6217.4 |
| HPLC Purity (%) | 81.3 | 80.6 |
| Acylation site (HPLC) | ε-amino group of Lys at position B29 | ε-amino group of Lys at position B29 |

*% yield corrected for purity of final material.

EXPERIMENT 1

Comparative Solubility Study of B29-N$^ε$-Arg$^{A0}$Gly$^{A21}$Arg$^{B31}$Arg$^{B32}$-Myristoyl Human Insulin Analog, Gly$^{A21}$Arg$^{B31}$Arg$^{B32}$Human Insulin Analog, and Arg$^{A0}$Gly$^{A21}$Arg$^{B31}$Arg$^{B32}$Human Insulin Analog A stock solution of B29-N$^ε$-Arg$^{A0}$Gly$^{A21}$Arg$^{B31}$Arg$^{B32}$-myristoyl human insulin analog was prepared by dissolving 7.5 mg of the polypeptide in 5.3094 g of a 2 mM glycine, sodium borate, and sodium citrate buffer solution at a pH of 9. The resulting solution was hazy and had a pH of 8.59. The pH was adjusted by adding 130 μL of 0.1N NaOH to give a visually clear solution with a final pH of 9. The resulting solution was passed through a 0.2 micron syringe filter. The filtered stock solution was characterized by UV spectroscopy so that the concentration of the peptide could be estimated. UV analysis indicated a concentration of 1.0589 mg/mL of the polypeptide.

A 160 μL portion of the stock solution was removed for serial dilution against water to provide a standard curve from HPLC analysis. Next, ten 350 μL samples were removed from the stock solution. The pH of these 10 samples were individually adjusted to a lower values by carefully adding 0.1N HCl. Table 4 indicates that the targeted and actual pH values of the pH adjusted samples.

After the pH of the last sample was adjusted, the samples were allowed to sit for 30 minutes at room temperature (23°–25° C.). The samples were then centrifuged at 14,000 rpm for 22 minutes and 300 μL of the supernatant was removed. The serial dilutions of stock and the pH adjusted samples were then analyzed by HPLC. Integration of the resulting chromatograms provided areas used to create a standard curve. The concentrations of sample remaining in solution were calculated from the standard curve. The mg/ml estimates were converted to percent of the polypeptide in solution relative to the UV spectroscopy estimates of the stock solution concentration. Table 5 presents the data that was obtained in the solubility study of B29-N$^ε$-Arg$^{A0}$Gly$^{A21}$Arg$^{B31}$Arg$^{B32}$-myristoyl Human Insulin Analog and FIG. 1 illustrates the same data in graphical form. The data indicates that the solubility of the acylated human insulin analog of this study decreases significantly when the pH drops below pH 8.66 and does not increase until the pH decreases below about a pH of 4.5.

As shown in Table 5, the B29—analog was found to be at least about 96% insoluble at a pH range of between pH 4.47 and 7.63.

TABLE 4

Summary of Target and Actual pH values for Sample solutions

| Sample | 1 | 2 | 3 | 4 | 5 |
|---|---|---|---|---|---|
| target pH | 8.5 | 8 | 7.5 | 7 | 6.5 |
| actual pH | 8.66 | 8.02 | 7.63 | 6.82 | 6.35 |
| Sample | 6 | 7 | 8 | 9 | 10 |
| target pH | 6 | 5.5 | 5 | 4.5 | 4 |
| actual pH | 5.86 | 5.55 | 5.08 | 4.47 | 3.85 |

TABLE 5

Summary of Solubility Data for B29-$N^\epsilon$-$Arg^{A0}Gly^{A21}Arg^{B31}Arg^{B32}$-Myristoyl Human Insulin Analog

| PH | Total Integrated Area | Calculated mg/ml in solution | Percent Calculated mg/ml |
|---|---|---|---|
| 9 | 22757.54 | 1.066 | 100.63 |
| 8.66 | 22221.79 | 1.041 | 98.33 |
| 8.02 | 10732.09 | 0.517 | 48.86 |
| 7.63 | 114.78 | 0.033 | 3.15 |
| 6.82 | 16.7 | 0.029 | 2.73 |
| 6.35 | 16.66 | 0.029 | 2.73 |
| 5.86 | 16.11 | 0.029 | 2.73 |
| 5.55 | 15.52 | 0.029 | 2.73 |
| 5.08 | 17.73 | 0.029 | 2.74 |
| 4.47 | 53.09 | 0.031 | 2.89 |
| 3.85 | 19544.35 | 0.919 | 86.80 |

Figure 2:
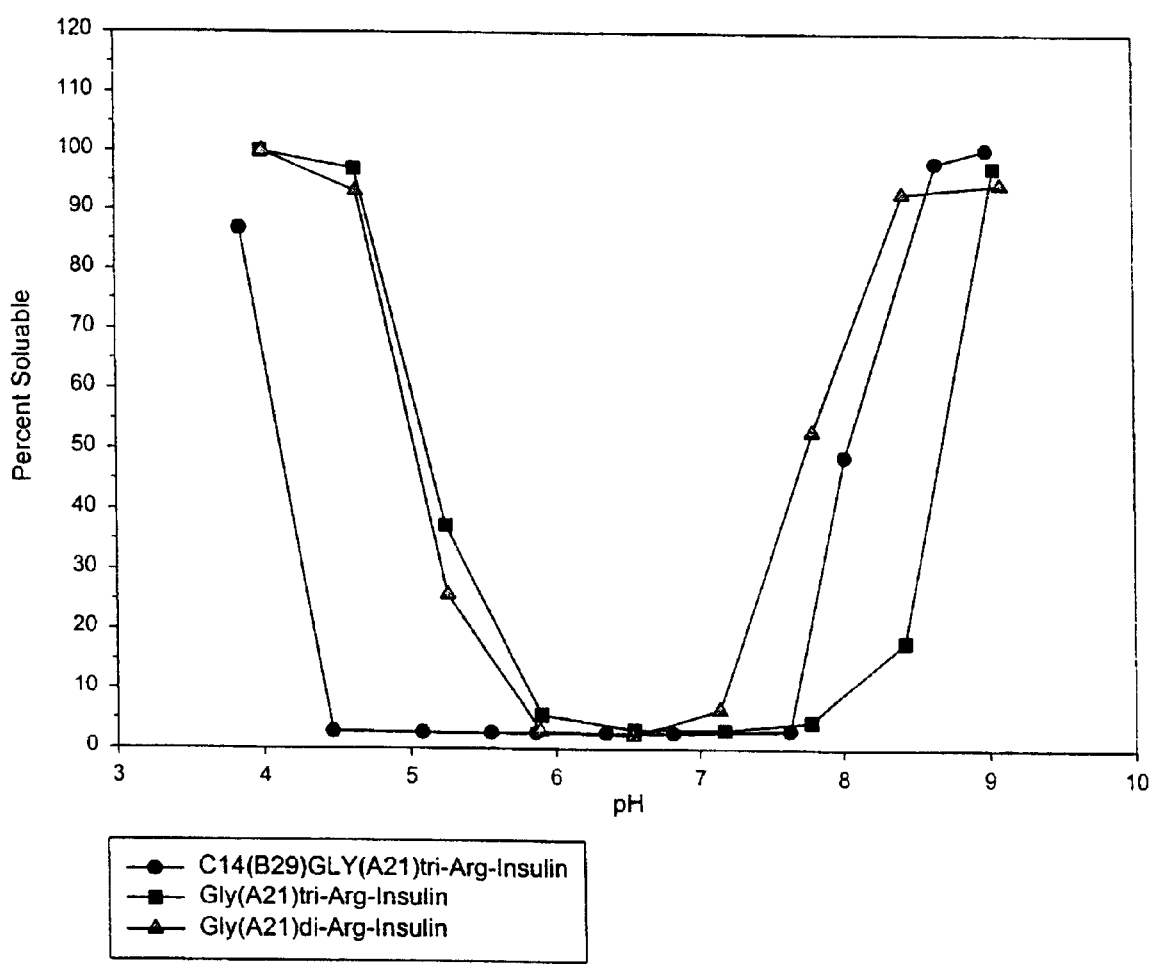
FIG. 2 is a graph comparing the solubilities of B29-N$^\epsilon$-Arg$^{A0}$Gly$^{A21}$Arg$^{B31}$Arg$^{B32}$-myristoyl human insulin analog, Gly$^{A21}$Arg$^{B31}$Arg$^{B32}$human insulin analog, and Arg$^{A0}$Gly$^{A21}$Arg$^{B31}$Arg$^{B32}$human insulin analog as a function of pH.

Solubility studies were performed on unacylated tri-arginine ($Arg^{A0}Gly^{A21}Arg^{B31}Arg^{B32}$) and di-arginine ($Gly^{A21}Arg^{B31}Arg^{B32}$) human insulin analogs using the same techniques as outlined above in order to obtain comparative data. The results form these studies are reproduced in table 6 and are graphically presented in FIG. 2.

TABLE 6

Summary of Solubility Data for $Arg^{A0}Gly^{A21}Arg^{B31}Arg^{B32}$-Human Insulin Analog and $Gly^{A21}Arg^{B31}Arg^{B32}$-Human Insulin Analog

| PH | % soluble $Arg^{A0}Gly^{A21}Arg^{B31}Arg^{B32}$ Human Insulin Analog | pH | % soluble $Gly^{A21}Arg^{B31}Arg^{B32}$ Human Insulin Analog |
|---|---|---|---|
| 9.05 | 97.62 | 9.10 | 94.64 |
| 8.43 | 18.11 | 8.43 | 93.04 |
| 7.78 | 4.63 | 7,80 | 52.90 |
| 7.17 | 3.27 | 7.14 | 6.52 |
| 6.55 | 3.34 | 6.54 | 2.28 |
| 5.90 | 5.58 | 5.89 | 3.01 |
| 5.25 | 37.27 | 5.26 | 25.83 |
| 4.64 | 97.03 | 4.65 | 93.11 |
| 4.00 | 100.00 | 4.01 | 100.00 |

EXPERIMENT 2

In Vivo Testing—Comparative Testing of Humulin® NPH, B29-$N^\epsilon$-myristoyl human insulin, B29-$N^\epsilon$-$Arg^{A0}Gly^{A21}Arg^{B31}Arg^{B32}$-myristoyl human insulin analog, and B29-$N^\epsilon$-$Gly^{A21}Arg^{B31}Arg^{B32}$-myristoyl human insulin analog in Pigs A formulation of B29-$N^\epsilon$-myristoyl human insulin was prepared by first dissolving a measured sample of the acylated human insulin in 0.1N HCl to provide a theoretical concentration of about 0.8 mg/mL. A UV spectrum was collected on a Hewlett-Packard HP8452A photodiode array spectrophotometer using a quartz cuvett with a 1 cm optical pathlength. A background spectrum of 0.1N HCl was arithmetically subtracted from the sample spectrum, and a correction for light scattering effects was made by subtracting the absorption value at 322 nm from that at 276 nm. The concentration of the myristoylated human insulin stock solution was calculated suing a theoretical extinction co-efficient and the absorption value at 276 nm. This concentration was in turn used to calculate the amount of a ZnO stock solution to add to the myristoylated human insulin such that the molar ration of Zn to insulin monomer was 0.35. Next, the pH of the myristoylated human insulin was carefully raised to 7.78 with 0.1N NaOH noting the volume that was required. Finally, the volume of myristoylated human insulin required to give approximately 3.61 mg per vial after lyophilization was injected into vials and freeze-dried.

A formulation of B29-$N^\epsilon$-myristoyl human insulin was prepared for study in pigs by reconstituting vials containing freeze-dried B29-$N^\epsilon$-myristoyl human insulin estimated to contain 3.58 mg of the acylated human insulin prepared as described above and 0.35 moles ZnO/mole of acylated insulin. The vials were reconstituted with 991 $\mu$L of a diluent with a pH of 7.5 and containing 7 mM monobasic sodium phosphate, 16 mg/mL glycerin and 5 mg/mL phenol. After reconstitution, the pH was measured and determined to be between 7.5 and 7.6.

A commercial formulation of Humulin® NPH was used. The commercial formulation contained: 600 $\mu$M zinc-human insulin crystals in aqueous solution containing 16 mg/ml glycerol, 25 $\mu$g/ml Zn, 0.73 mg/mi phenol, 1.6 mg/ml m-cresol, 0.35 mg/ml protamine sulfate, and 3.78 mg/ml dibasic sodium phosphate. Humulin® NPH and Humulin® N are terms used to identify the same insulin material.

A formulation of B29-$N^\epsilon$-$Arg^{A0}Gly^{A21}Arg^{B31}Arg^{B32}$-myristoyl human insulin analog was prepared containing 311 $\mu$M of monoacylated tri-arginine insulin analog in an aqueous solution of 16 mg/ml glycerol, 80 $\mu$g/ml Zn, and 2.5 mg/ml m-cresol at a pH of 3.06.

A formulation of B29-$N^\epsilon$-$Gly^{A21}Arg^{B31}Arg^{B32}$-myristoyl human insulin analog was prepared containing 825 $\mu$M of the monoacylated di-arginine insulin analog in an aqueous solution of 16 mg/ml glycerol, 80 $\mu$g/mil Zn, and 2.5 mg/ml m-cresol at a pH 3.03.

Studies were performed in young (3–4 months of age), conscious, chronically catheterized, female pigs weighing 15–25 kg after a 22–24 hour fast. Somatostatin (0.3 mg/kg/min.) was infused through one of two implanted jugular catheters to suppress endogenous pancreatic secretion [see, e.g. Radziuk, J., et al. *Diabetes* 46:548 (1997)]. Fifteen minutes after initiation of the somatostatin infusion, insulin analogs were injected subcutaneously (6 nmol/kg) in the soft skin directly behind the ear. Eight pigs were used—one pig was treated with of B29-N$^\epsilon$-Gly$^{A21}$Arg$^{B31}$Arg$^{B32}$-myristoyl human insulin analog, one pig was treated with B29-N$^\epsilon$-Arg$^{A0}$Gly$^{A21}$Arg$^{B31}$Arg$^{B32}$-myristoyl human insulin analog, three pigs were treated with Humulin® NPH, and three pigs were treated with B29-N$^\epsilon$-myristoyl human insulin. For each experiment, arterial blood samples were taken intermittently for up to 14 hours post-injection to monitor the pharmacodynamics and the pharmacokinetics of the insulin analog. Glucose was infused as needed through a second implanted jugular catheter to maintain the plasma glucose concentration near basal throughout the experiment. Glucose concentrations were determined the day of the study using a glucose oxidase method in either a YSI Glucose/Lactate Analyzer (Yellow Springs, Ohio.) or a Beckman Glucose Analyzer II (Fullerton, Calif.). Insulin concentrations were determined at a later date using a double antibody radioimmunoassay (rat insulin antibody from Linco Research, St. Charles, Mo.).

Plots were made of the glucose infusion rates for each analog versus time, and the cumulative glucose infused, for each analog, versus time. Historical data (collected following the same protocol) for Humulin® NPH (n=3) and B29-N$^\epsilon$-myristoyl human insulin (n=3) are co-plotted as well.

Cumulative Glucose Infusion

Figure 3:
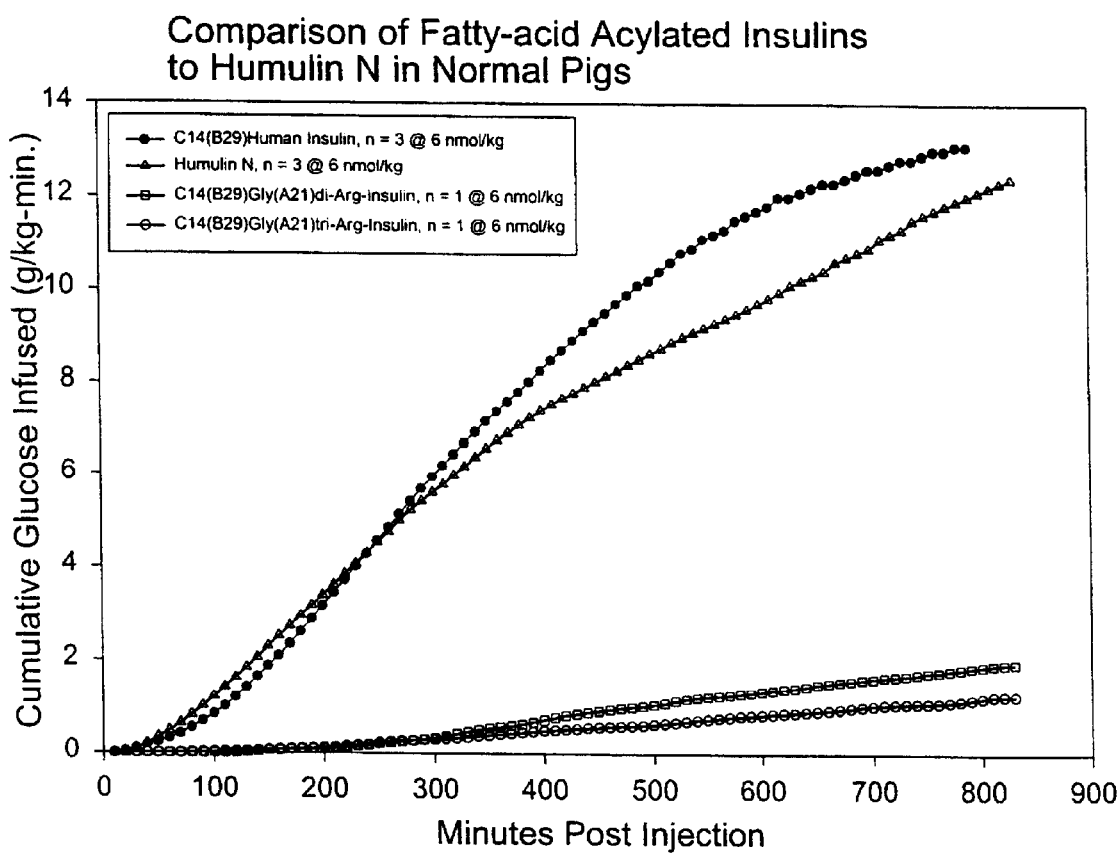
FIG. 3 is a graph comparing cumulative glucose infused versus time in normal pigs after subcutaneously administering 6 nmol/kg of various insulins including Humulin® NPH, B29-N$^\epsilon$-myristoyl human insulin, B29-N$^\epsilon$-Arg$^{A0}$Gly$^{A21}$Arg$^{B31}$Arg$^{B32}$-myristoyl human insulin analog, and B29-N$^\epsilon$-Gly$^{A21}$Arg$^{B31}$Arg$^{B32}$-myristoyl human insulin analog.

FIG. 3 is a graph comparing cumulative glucose infused versus time in an experiment treating normal pigs with equal amounts of four compounds including Humulin® NPH, B29-N$^\epsilon$-myristoyl human insulin, B29N$^\epsilon$-Arg$^{A0}$Gly$^{A21}$Arg$^{B31}$Arg$^{B32}$-myristoyl human insulin analog, and B29-N$^\epsilon$-Gly$^{A21}$Arg$^{B31}$Arg$^{B32}$-myristoyl human insulin analog. The data plotted in FIG. 3 represents the total amount of glucose infused during the experiment. The data show that both B29-N$^{\epsilon\text{-}ArgA0}$Gly$^{A21}$Arg$^{B31}$Arg$^{B32}$-myristoyl human insulin analog, and B29-N$^{\epsilon\text{-}GlyA21}$Arg$^{B31}$Arg$^{B32}$-myristoyl human insulin analog resulted in glucose uptake, but at dramatically lower levels relative to Humulin® NPH or B29-N$^\epsilon$-myristoyl human insulin. The results are consistent with a delay of insulin analog activity based on their designed physical characteristics—precipitation at physiological pH and binding to serum albumin. Generally, one can determine the duration of activity of a given insulin or insulin analog preparation by examining the time at which the value for the cumulative glucose infused reaches a plateau. The experiments performed here were of 14 hour duration, but this period was not long enough to determine the end points for any of the four species under investigation, but one of ordinary skill can see that B29-N$^\epsilon$-myristoyl human insulin has started to plateau and is therefore close to the end of its activity. Based on these results, it is expected that the inventive analogs will have longer duration of activity than Humulin NPH.

Plasma Levels of Humulin ® and Analogs

Figure 4:
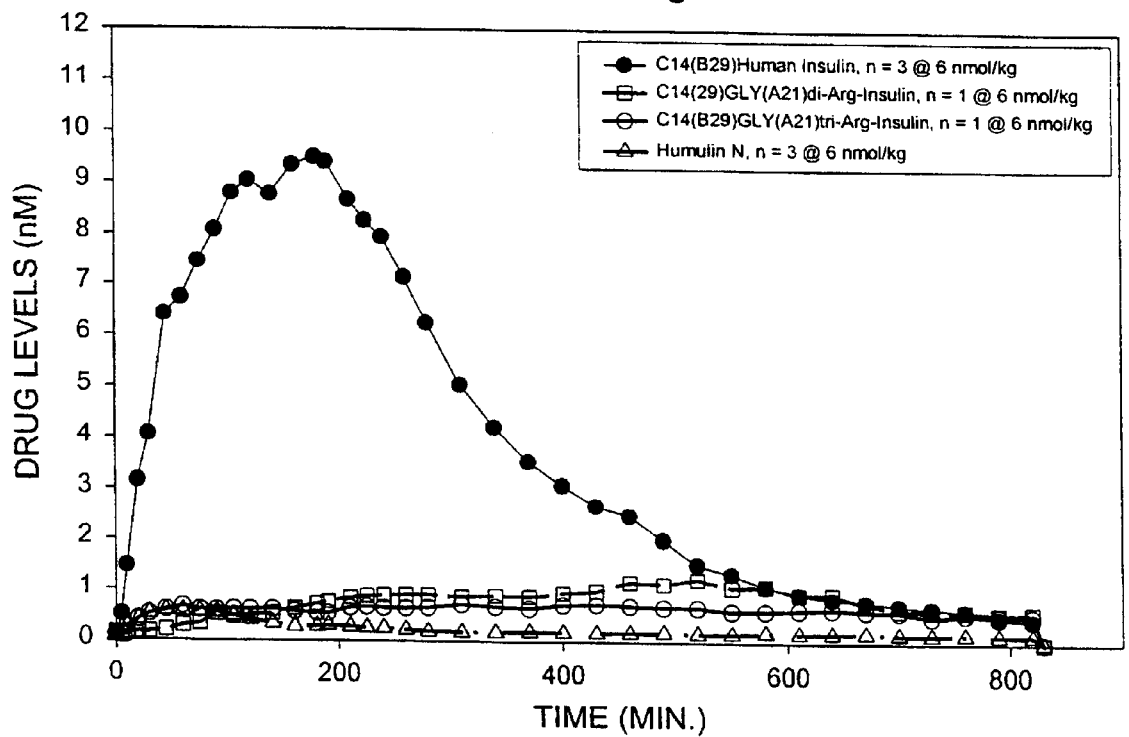
FIG. 4 is a graph comparing plasma levels of various insulins in normal pigs after subcutaneously administering 6 nmol/kg of Humulin® NPH, B29-N$^\epsilon$-myristoyl human insulin, B29-N$^\epsilon$-Arg$^{A0}$Gly$^{A21}$Arg$^{B31}$Arg$^{B32}$-myristoyl human insulin analog, and B29-N$^\epsilon$-Gly$^{A21}$Arg$^{B31}$Arg$^{B32}$myristoyl human insulin analog.

FIG. 4 is a graph comparing plasma levels of the four compounds in normal pigs. Humulin® NPH, B29-N$^\epsilon$-myristoyl human insulin, B29-N$^\epsilon$-Arg$^{A0}$Gly$^{A21}$Arg$^{B31}$Arg$^{B32}$-myristoyl human insulin analog, and B29-N$^\epsilon$-Gly$^{A21}$Arg$^{B31}$Arg$^{B32}$-myristoyl human insulin analog were the compounds used in the study. The data shows that Humulin® NPH has a peak blood level of approximately 0.5 nM between 0 and 150 minutes post subcutaneous injection, and then maintains a fairly constant level at 0.25 nM for the rest of the experiment. B29-N$^\epsilon$-Gly$^{A21}$Arg$^{B31}$Arg$^{B32}$-myristoyl human insulin analog shows a slow build up of drug level until 200 minutes, after which it remains constant until approximately 400 minutes, at which point it shows a broad peak of activity that settles down at approximately 700 minutes. B29-N$^\epsilon$-Arg$^{A0}$Gly$^{A21}$Arg$^{B31}$Arg$^{B32}$-myristoyl human insulin analog shows an onset of drug level similar to that for Humulin® NPH, but maintains a level between 0.6 and 0.7 nM from approximately 50 minutes to the end of the experiment with no indication that the level would decay anytime soon. The drug levels of B29-N$^\epsilon$-myristoyl human insulin were approximately 18 times higher than Humulin® NPH, B29N$^\epsilon$Arg$^{A0}$Gly$^{A21}$Arg$^{B31}$Arg$^{B32}$-myristoyl human insulin analog, and B29-N$^{\epsilon\text{-}GlyA21}$Arg$^{B31}$Arg$^{B32}$-myristoyl human insulin analog drug levels at 100 minutes, reflecting albumin-bound insulin. Radzuik, J. *Diabetologica* 41:116 (1998). This demonstrates the ability of B29-N$^\epsilon$-myristoyl human insulin enhanced ability of this species to bind to serum albumin. In both the myristoylated di-arginine and tri-arginine analogs, the drug levels were noticeably higher than Humulin® NPH from 100 minutes to the end of the experiment. However, the drug levels of B29-N$^\epsilon$-Arg$^{A0}$Gly$^{A21}$Arg$^{B31}$Arg$^{B32}$-myristoyl human insulin analog, and B29-N$^\epsilon$-Gly$^{A21}$Arg$^{B31}$Arg$^{B32}$-myristoyl human insulin analog were appreciably lower than those for B29-N$^\epsilon$-myristoyl human insulin from the start of the experiment until approximately 600 minutes.

Glucose Infusion Rates

Figure 5:
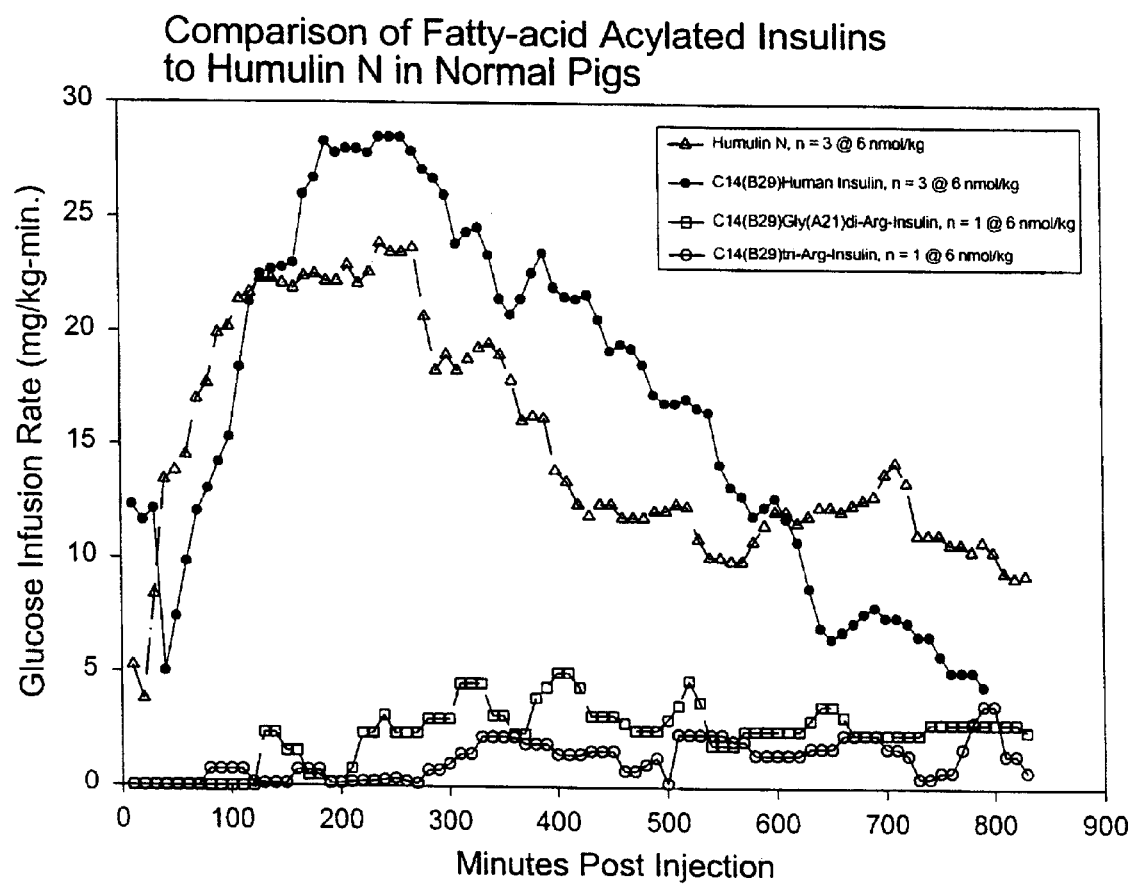
FIG. 5 is a graph comparing the rates at which glucose was infused to maintain euglycemia for various insulins in normal female pigs after subcutaneously administering 6 nmol/kg of Humulins® NPH, B29-N$^\epsilon$-myristoyl human insulin, B29-N$^\epsilon$-Arg$^{A0}$Gly$^{A21}$Arg$^{B31}$Arg$^{B32}$-myristoyl human insulin analog, and B29-N$^\epsilon$-Gly$^{A21}$Arg$^{B31}$Arg$^{B32}$-myristoyl human insulin analog.

FIG. 5 is a graph comparing the rates at which glucose was infused to maintain euglycemia for various insulins in normal female pigs. The compounds used were Humulin® NPH, B29-N$^\epsilon$-myristoyl human insulin, B29-N$^{\epsilon\text{-}}$Arg$^{A0}$Gly$^{A21}$Arg$^{B31}$Arg$^{B32}$-myristoyl human insulin analog, and B29-N$^\epsilon$-Gly$^{A21}$Arg$^{B31}$Arg$^{B32}$-myristoyl human insulin analog. The plotted data demonstrates that the fatty-acid acylated analogs with shifted isoelectric points possess insulin-like activity in normal, female pigs. Each analog resulted in a flat activity profile when compared to Humulin® NPH or B29-N$^\epsilon$-myristoyl human insulin (note that the B29-N$^\epsilon$-myristoyl human insulin is designed to bind to serum albumin to afford protracted time action). The level of glucose turn-over rate of B29-N$^\epsilon$-Arg$^{A0}$Gly$^{A21}$Arg$^{B31}$Arg$^{B32}$-myristoyl human insulin analog, and B29-N$^\epsilon$-Gly$^{A21}$Arg$^{B31}$Arg$^{B32}$-myristoyl human insulin analog was in the range of 2–3 mg/kg/minute. Humulin® NPH and B29-N$^\epsilon$-myristoyl human insulin, on the other hand, show definite peaks in their glucose turn-over rate of 25 and 30 mg/kg/minute respectively, and maintain much higher turn-over rates throughout the experiment. Addtionally, Humulin NPH maintains a higher turn-over rate throughout the experiment than do the acylated Gly$^{A21}$tri-arginine and Gly$^{A21}$di-arginine species.

The goal of a basal insulin formulation is to cover only hepatic glucose output over time. Hepatic glucose output typically ranges form 2–3 mg/kg/minute. Thus, the turn-over rates for Humulin® NPH and B29-N$^\epsilon$-myristoyl human insulin exceed the turn-over rate desired for a basal insulin. As a result, Humulin® NPH and B29-N$^\epsilon$-myristoyl human insulin could produce a condition of hypoglycemia. As, FIG. 5 shows, B29-N$^{\epsilon\text{-}ArgA0}$Gly$^{A21}$Arg$^{B31}$Arg$^{B32}$-myristoyl human insulin analog, and B29-N$^{\epsilon\text{-}GlyA21}$Arg$^{B31}$Arg$^{B32}$-myristoyl human insulin analog have turn-over rates that are consistent with those required for an excellent basal insulin formulation.

At no time did either B29-N$^\epsilon$-Arg$^{A0}$Gly$^{A21}$Arg$^{B31}$Arg$^{B32}$-myristoyl human insulin analog or B29-N$^{\epsilon\text{-}}$Gly$^{A21}$Arg$^{B31}$Arg$^{B32}$-myristoyl human insulin analog show any peaks in terms of glucose infusion rates or plasma drug levels. The lower turn-over rates of these novel species are expected to cover the basal hepatic glucose output, while producing less incidences of hypoglycemia. Thus, the myristoylated Gly21-di-arginine and Gly21-tri-arginine species are expected to have a greater therapeutic index than that of Humulin® NPH. Thus, one would predict that myristoylated Gly-di and tri arginine species have a greater therapeutic index than Humulin NPH.

SEQUENCE LISTING

<160> NUMBER OF SEQ ID NOS: 15

<210> SEQ ID NO 1
<211> LENGTH: 22
<212> TYPE: PRT
<213> ORGANISM: Homo sapiens
<220> FEATURE:
<221> NAME/KEY: VARIANT
<222> LOCATION: (1)
<223> OTHER INFORMATION: Xaa is Arg or absent
<221> NAME/KEY: VARIANT
<222> LOCATION: (22)
<223> OTHER INFORMATION: Xaa is any naturally occurring amino acid
      except Cys or Lys

<400> SEQUENCE: 1

Xaa Gly Ile Val Glu Gln Cys Cys Thr Ser Ile Cys Ser Leu Tyr Gln
 1               5                  10                  15

Leu Glu Asn Tyr Cys Xaa
            20

<210> SEQ ID NO 2
<211> LENGTH: 32
<212> TYPE: PRT
<213> ORGANISM: Homo sapiens
<220> FEATURE:
<221> NAME/KEY: VARIANT
<222> LOCATION: (3)
<223> OTHER INFORMATION: Xaa is any naturally occurring amino acid
      except Cys or Lys
<221> NAME/KEY: VARIANT
<222> LOCATION: (27)
<223> OTHER INFORMATION: Xaa is Thr or absent
<221> NAME/KEY: VARIANT
<222> LOCATION: (28)
<223> OTHER INFORMATION: Xaa is Pro, Leu, Val, Ala, Lys or Asp
<221> NAME/KEY: VARIANT
<222> LOCATION: (29)
<223> OTHER INFORMATION: Xaa is Pro or Lys
<221> NAME/KEY: VARIANT
<222> LOCATION: (30)
<223> OTHER INFORMATION: Xaa is absent or any naturally occurring amino
      acid except Cys or Lys

<400> SEQUENCE: 2

Phe Val Xaa Gln His Leu Cys Gly Ser His Leu Val Glu Ala Leu Tyr
 1               5                  10                  15

Leu Val Cys Gly Glu Arg Gly Phe Phe Tyr Xaa Xaa Xaa Xaa Arg Arg
            20                  25                  30

<210> SEQ ID NO 3
<211> LENGTH: 4
<212> TYPE: PRT
<213> ORGANISM: Homo sapiens

<400> SEQUENCE: 3

Gly Gln Arg Arg
 1

<210> SEQ ID NO 4
<211> LENGTH: 4
<212> TYPE: PRT
<213> ORGANISM: Homo sapiens

```
<400> SEQUENCE: 4

Arg Gly Arg Arg
 1

<210> SEQ ID NO 5
<211> LENGTH: 5
<212> TYPE: PRT
<213> ORGANISM: Homo sapiens

<400> SEQUENCE: 5

Arg Gly Gln Arg Arg
 1               5

<210> SEQ ID NO 6
<211> LENGTH: 5
<212> TYPE: PRT
<213> ORGANISM: Homo sapiens

<400> SEQUENCE: 6

Arg Gly Asp Arg Arg
 1               5

<210> SEQ ID NO 7
<211> LENGTH: 5
<212> TYPE: PRT
<213> ORGANISM: Homo sapiens

<400> SEQUENCE: 7

Gly Lys Pro Arg Arg
 1               5

<210> SEQ ID NO 8
<211> LENGTH: 6
<212> TYPE: PRT
<213> ORGANISM: Homo sapiens

<400> SEQUENCE: 8

Gly Gln Lys Pro Arg Arg
 1               5

<210> SEQ ID NO 9
<211> LENGTH: 6
<212> TYPE: PRT
<213> ORGANISM: Homo sapiens

<400> SEQUENCE: 9

Arg Gly Lys Pro Arg Arg
 1               5

<210> SEQ ID NO 10
<211> LENGTH: 7
<212> TYPE: PRT
<213> ORGANISM: Homo sapiens

<400> SEQUENCE: 10

Arg Gly Gln Lys Pro Arg Arg
 1               5

<210> SEQ ID NO 11
<211> LENGTH: 7
<212> TYPE: PRT
<213> ORGANISM: Homo sapiens

<400> SEQUENCE: 11
```

-continued

```
Arg Gly Asp Lys Pro Arg Arg
 1               5

<210> SEQ ID NO 12
<211> LENGTH: 4
<212> TYPE: PRT
<213> ORGANISM: Homo sapiens

<400> SEQUENCE: 12

Lys Pro Arg Arg
 1

<210> SEQ ID NO 13
<211> LENGTH: 5
<212> TYPE: PRT
<213> ORGANISM: Homo sapiens

<400> SEQUENCE: 13

Arg Lys Pro Arg Arg
 1               5

<210> SEQ ID NO 14
<211> LENGTH: 56
<212> TYPE: PRT
<213> ORGANISM: Homo sapiens
<220> FEATURE:
<221> NAME/KEY: VARIANT
<222> LOCATION: (1)
<223> OTHER INFORMATION: Xaa is hydrogen or a peptide from 1 to about
      100 amino acids that has either Lys or Arg at its C-terminal
      amino acid
<221> NAME/KEY: VARIANT
<222> LOCATION: (4)
<223> OTHER INFORMATION: Xaa is any naturally occurring amino acid
      except Cys or Lys
<221> NAME/KEY: VARIANT
<222> LOCATION: (28)
<223> OTHER INFORMATION: Xaa is Thr or absent
<221> NAME/KEY: VARIANT
<222> LOCATION: (29)
<223> OTHER INFORMATION: Xaa is Pro, Leu, Val, Ala, Lys or Asp
<221> NAME/KEY: VARIANT
<222> LOCATION: (30)
<223> OTHER INFORMATION: Xaa is Pro or Lys
<221> NAME/KEY: VARIANT
<222> LOCATION: (31)
<223> OTHER INFORMATION: Xaa is absent or any naturally occurring amino
      acid except Cys or Lys
<221> NAME/KEY: VARIANT
<222> LOCATION: (34)
<223> OTHER INFORMATION: Xaa is a peptide from 1 to about 35 amino
      acids, none of which is Cys, wherein the C-terminal amino acid is
      Lys or Arg
<221> NAME/KEY: VARIANT
<222> LOCATION: (35)
<223> OTHER INFORMATION: Xaa is Arg or absent
<221> NAME/KEY: VARIANT
<222> LOCATION: (56)
<223> OTHER INFORMATION: Xaa is any naturally occurring amino acid
      except Cys or Lys

<400> SEQUENCE: 14

Xaa Phe Val Xaa Gln His Leu Cys Gly Ser His Leu Val Glu Ala Leu
 1               5                  10                  15

Tyr Leu Val Cys Gly Glu Arg Gly Phe Phe Tyr Xaa Xaa Xaa Xaa Arg
                20                  25                  30

Arg Xaa Xaa Gly Ile Val Glu Gln Cys Cys Thr Ser Ile Cys Ser Leu
        35                  40                  45

Tyr Gln Leu Glu Asn Tyr Cys Xaa
```

```
<210> SEQ ID NO 15
<211> LENGTH: 56
<212> TYPE: PRT
<213> ORGANISM: Homo sapiens
<220> FEATURE:
<221> NAME/KEY: VARIANT
<222> LOCATION: (1)
<223> OTHER INFORMATION: Xaa is hydrogen or a peptide from 1 to about
      100 amino acids that has either Lys or Arg at its C-terminal
      amino acid
<221> NAME/KEY: VARIANT
<222> LOCATION: (2)
<223> OTHER INFORMATION: Xaa is Arg or absent
<221> NAME/KEY: VARIANT
<222> LOCATION: (23)
<223> OTHER INFORMATION: Xaa is any naturally occurring amino acid
      except Cys or Lys
<221> NAME/KEY: VARIANT
<222> LOCATION: (24)
<223> OTHER INFORMATION: Xaa is a peptide from 1 to about 35 amino
      acids, none of which is Cys, wherein the C-terminal amino acid is
      Lys or Arg
<221> NAME/KEY: VARIANT
<222> LOCATION: (27)
<223> OTHER INFORMATION: Xaa is any naturally occurring amino acid
      except Cys or Lys
<221> NAME/KEY: VARIANT
<222> LOCATION: (51)
<223> OTHER INFORMATION: Xaa is Thr or absent
<221> NAME/KEY: VARIANT
<222> LOCATION: (52)
<223> OTHER INFORMATION: Xaa is Pro, Leu, Val, Ala, Lys or Asp
<221> NAME/KEY: VARIANT
<222> LOCATION: (53)
<223> OTHER INFORMATION: Xaa is Pro or Lys
<221> NAME/KEY: VARIANT
<222> LOCATION: (54)
<223> OTHER INFORMATION: Xaa is absent or any naturally occurring amino
      acid except Cys or Lys

<400> SEQUENCE: 15

Xaa Xaa Gly Ile Val Glu Gln Cys Cys Thr Ser Ile Cys Ser Leu Tyr
 1               5                  10                  15

Gln Leu Glu Asn Tyr Cys Xaa Xaa Phe Val Xaa Gln His Leu Cys Gly
            20                  25                  30

Ser His Leu Val Glu Ala Leu Tyr Leu Val Cys Gly Glu Arg Gly Phe
        35                  40                  45

Phe Tyr Xaa Xaa Xaa Xaa Arg Arg
        50                  55
```

What is claimed is:

1. A fatty acid-acylated insulin analog comprising an insulin analog to which a fatty acyl chain is joined by an amide bond, wherein said fatty insulin analog has an isoelectric point that is higher than the isoelectric point of insulin.

2. The fatty acid-acylated insulin analog according to claim 1, wherein said fatty acid-acylated insulin analog has at least one more net positive charge than insulin.

3. The fatty acid-acylated insulin analog according to claim 1, wherein said fatty acid-acylated insulin analog has at least two more net positive charges than insulin.

4. A mono-acylated insulin analog, comprising:

(a) a polypeptide of SEQ ID NO:1 properly crosslinked to a polypeptide of SEQ ID NO:2, or a pharmaceutically acceptable salt thereof, wherein the polypeptide of SEQ ID NO:1 has the sequence:

```
      0   1           5                  10                  15
      Xaa Gly Ile Val Glu Gln Cys Cys Thr Ser Ile Cys Ser Leu Tyr Gln Leu  (SEQ ID NO:1)
                  20
      Glu Asn Tyr Cys Xaa
``` wherein:
Xaa at position 0 is either Arg or absent; and
Xaa at position 21 is any naturally occurring amino acid except Cys and Lys; and
the polypeptide of SEQ ID NO:2 has the sequence:

```
1               5                   10                  15
Phe Val Xaa Gln His Leu Cys Gly Ser His Leu Val Glu Ala Leu Tyr    (SEQ ID NO:2)

20                  25                  30
Leu Val Cys Gly Glu Arg Gly Phe Phe Tyr Xaa Xaa Xaa Xaa Arg Arg
``` wherein:
Xaa at position 3 is any naturally occurring amino acid except Cys and Lys;
Xaa at position 27 is either Thr or absent;
Xaa at position 28 is selected from the group consisting of Pro, Leu, Val, Ala, Lys, and Asp;
Xaa at position 29 is selected from the group consisting of Pro and Lys;
Xaa at position 30 is absent or any naturally occurring amino acid except Cys or Lys;
further wherein position 28 or position 29 is Lys, and if position 28 is Lys, position 29 is not Lys; and
(b) Lys at position 28 or position 29 of SEQ ID NO:2 is acylated.

5. The mono-acylated insulin analog of claim 4, wherein the polypeptide is selected from the group consisting of: the polypeptide wherein Xaa at position 30 of the polypeptide of SEQ ID NO:2 is Thr; the polypeptide wherein Xaa at position 21 of the polypeptide of SEQ ID NO:1 is Asn; the polypeptide wherein Xaa at position 3 of the polypeptide of SEQ ID NO:2 is Asn; the polypeptide wherein Xaa at position 21 of the polypeptide of SEQ ID NO:1 is Gly and Xaa at position 3 of the polypeptide of SEQ ID NO:2 is Gln; and the polypeptide wherein Xaa at position 21 of the polypeptide of SEQ ID NO:1 is Gly and Xaa at position 3 of the polypeptide of SEQ ID NO:2 is Asp.

6. The mono-acylated insulin analog of claim 4, wherein Xaa at position 21 of the polypeptide of SEQ ID NO:1 is Asn, and wherein Xaa at position 3 of the polypeptide of SEQ ID NO:2 is Asn.

7. The mono-acylated insulin analog of claim 6, wherein the polypeptide is selected from the group consisting of: the polypeptide wherein Xaa at position 28 of the polypeptide of SEQ ID NO:2 is Pro and Xaa at position 29 of the polypeptide of SEQ ID NO:2 is Lys; and the polypeptide wherein Xaa at position 28 of the polypeptide of SEQ ID NO:2 is Lys and Xaa at position 29 of the polypeptide of SEQ ID NO:2 is Pro.

8. The mono-acylated insulin analog of claim 4, wherein Xaa at position 0 of the polypeptide of SEQ ID NO:1 is Arg.

9. The mono-acylated insulin analog of claim 8, wherein Xaa at position 21 of the polypeptide of SEQ ID NO:1 is selected from the group consisting of Gly, Asn, Ala, and Gln.

10. The mono-acylated insulin analog of claim 8, wherein Xaa at position 21 of the polypeptide of SEQ ID NO:1 is Gly, Xaa at position 3 of SEQ ID NO:2 is selected from the group consisting of Asn, Gln, and Asp; Xaa at position 27 of SEQ ID NO:2 is Thr; Xaa at position 28 of SEQ ID NO:2 is Pro; and Xaa at position 29 of SEQ ID NO:2 is Lys.

11. The mono-acylated insulin analog of claim 8, wherein Xaa at position 21 of the polypeptide of SEQ ID NO:1 is Asn, Xaa at position 3 of SEQ ID NO:2 is Asn; Xaa at position 27 of SEQ ID NO:2 is Thr, and Xaa at position 28 of SEQ ID NO:2 is Pro; and Xaa at position 29 of SEQ ID NO:2 is Lys.

12. The mono-acylated insulin analog of claim 8, wherein Xaa at position 21 of the polypeptide of SEQ ID NO:1 is Gly, Xaa at position 3 of SEQ ID NO:2 is selected from the group consisting of Asn, Gln, and Asp; Xaa at position 27 of SEQ ID NO:2 is Thr; Xaa at position 28 of SEQ ID NO:2 is Lys; and Xaa at position 29 of SEQ ID NO:2 is Pro.

13. The mono-acylated insulin analog of claim 8, wherein Xaa at position 21 of the polypeptide of SEQ ID NO:1 is Asn, Xaa at position 3 of SEQ ID NO:2 is Asn; Xaa at position 27 of SEQ ID NO:2 is Thr; Xaa at position 28 of SEQ ID NO:2 is Lys; and Xaa at position 29 of SEQ ID NO:2 is Pro.

14. The mono-acylated insulin analog of claim 4, wherein Xaa at position 0 of the polypeptide of SEQ ID NO:1 is absent.

15. The mono-acylated insulin analog of claim 14, wherein Xaa at position 21 of the polypeptide of SEQ ID NO:1 is selected from the group consisting of Gly, Asn, Ala, and Gln.

16. The mono-acylated insulin analog of claim 14, wherein Xaa at position 21 of the polypeptide of SEQ ID NO:1 is Gly, Xaa at position 3 of SEQ ID NO:2 is selected from the group consisting of Asn and Gln; Xaa at position 27 of SEQ ID NO:2 is Thr; Xaa at position 28 of SEQ ID NO:2 is Pro; and Xaa at position 29 of SEQ ID NO:2 is Lys.

17. The mono-acylated insulin analog of claim 14, wherein Xaa at position 21 of the polypeptide of SEQ ID NO:1 is Asn, Xaa at position 3 of SEQ ID NO:2 is Asn; Xaa at position 27 of SEQ ID NO:2 is Thr; Xaa at position 28 of SEQ ID NO:2 is Pro; and Xaa at position 29 of SEQ ID NO:2 is Lys.

18. The mono-acylated insulin analog of claim 14, wherein Xaa at position 21 of the polypeptide of SEQ ID NO:1 is Gly, Xaa at position 3 of SEQ ID NO:2 is selected from the group consisting of Asn and Gln; Xaa at position 27 of SEQ ID NO:2 is Thr; Xaa at position 28 of SEQ ID NO:2 is Lys; and Xaa at position 29 of SEQ ID NO:2 is Pro.

19. The mono tcylated insulin analog of claim 14, wherein Xaa at position 21 of the polypeptide of SEQ ID NO:1 is Asn, Xaa at position 3 of SEQ ID NO:2 is Asn; Xaa at position 27 of SEQ ID NO:2 is Thr; Xaa at position 28 of SEQ ID NO:2 is Lys; and Xaa at position 29 of SEQ ID NO:2 is Pro.

20. The mono-acylated insulin analog of claim 4, wherein the Lys at position 28 or position 29 of the polypeptide of SEQ ID NO:2 is acylated with a $C_4$–$C_{21}$ fatty acid.

21. The mono-acylated insulin analog of claim 4, wherein the Lys at position 28 or position 29 of the polypeptide of SEQ ID NO:2 is acylated with a fatty acid selected from the group consisting of palmitic, myristic, hexanoic, and octanoic acid.

22. A human insulin analog selected from the group consisting of
  a B29-$N^\epsilon$-Gly$^{A21}$Arg$^{B31}$Arg$^{B32}$-myristoyl human insulin analog,
  a B29-$N^\epsilon$-Gly$^{A21}$Gln$^{B3}$Arg$^{B31}$Arg$^{B32}$-myristoyl human insulin analog,
  a B29-$N^\epsilon$-Arg$^{A0}$Gly$^{A21}$Arg$^{B31}$Arg$^{B32}$-myristoyl human insulin analog, a B29-N$^\epsilon$-Arg$^{A0}$Gly$^{A21}$Gln$^{B3}$Arg$^{B31}$Arg$^{B32}$-myristoyl human insulin analog, a B29-N$^\epsilon$-Arg$^{A0}$Gly$^{A21}$Asp$^{B3}$Arg$^{B31}$Arg$^{B32}$-myristoyl human insulin analog, a B29-N$^\epsilon$-Arg$^{B31}$Arg$^{B32}$-myristoyl human insulin analog, a B29-N$^\epsilon$-Arg$^{A0}$Arg$^{B31}$Arg$^{B32}$-myristoyl human insulin analog, a B29-N$^\epsilon$-Gly$^{A21}$Arg$^{B31}$Arg$^{B32}$-octanoyl human insulin analog, a B29-N$^\epsilon$-Gly$^{A21}$Gln$^{B3}$Arg$^{B31}$Arg$^{B32}$-octanoyl human insulin analog, a B29-N$^\epsilon$-Arg$^{A0}$Gly$^{A21}$Arg$^{B31}$Arg$^{B32}$-octanoyl human insulin analog, a B29-N$^\epsilon$-Arg$^{A0}$Gly$^{A21}$Gln$^{B3}$Arg$^{B31}$Arg$^{B32}$-octanoy human insulin analog, a B29-N$^\epsilon$-Arg$^{A0}$Gly$^{A21}$Asp$^{B3}$Arg$^{B31}$Arg$^{B32}$-octanoyl human insulin analog, a B29-N$^\epsilon$-Arg$^{B31}$Arg$^{B32}$-octanoyl human insulin analog, a B29-N$^\epsilon$-Arg$^{A0}$Arg$^{B31}$Arg$^{B32}$-octanoyl human insulin analog, a B28-N$^\epsilon$-Gly$^{A21}$Lys$^{B28}$Pro$^{B29}$Arg$^{B31}$Arg$^{B32}$-myristoyl human insulin analog, a B28-N$^\epsilon$-Gly$^{A21}$Gln$^{B3}$Lys$^{B28}$Pro$^{B29}$Arg$^{B31}$Arg$^{B32}$-myristoyl human insulin analog, a B28-N$^\epsilon$-Arg$^{A0}$Gly$^{A21}$Lys$^{B28}$Pro$^{B29}$Arg$^{B31}$Arg$^{B32}$-myristoyl human insulin analog, a B28-N$^\epsilon$-Arg$^{A0}$Gly$^{A21}$Gln$^{B3}$Lys$^{B28}$Pro$^{B29}$Arg$^{B31}$Arg$^{B32}$-myristoyl human insulin analog, a B28-N$^\epsilon$-Arg$^{A0}$Gly$^{A21}$Asp$^{B3}$Lys$^{B28}$Pro$^{B29}$Arg$^{B31}$Arg$^{B32}$-myristoyl human insulin analog, a B28-N$^\epsilon$-Lys$^{B28}$Pro$^{B29}$Arg$^{B31}$Arg$^{B32}$-myristoyl human insulin analog, a B28-N$^\epsilon$-Arg$^{A0}$Lys$^{B28}$Pro$^{B29}$Arg$^{B31}$Arg$^{B32}$-myristoyl human insulin analog, a B28-N$^\epsilon$-Gly$^{A21}$Lys$^{B28}$Pro$^{B29}$Arg$^{B31}$Arg$^{B32}$-octanoyl human insulin analog, a B28-N$^\epsilon$-Gly$^{A21}$Gln$^{B3}$Lys$^{B28}$Pro$^{B29}$Arg$^{B31}$Arg$^{B32}$-octanoyl human insulin analog, a B28-N$^\epsilon$-Arg$^{A0}$Gly$^{A21}$Lys$^{B28}$Pro$^{B29}$Arg$^{B31}$Arg$^{B32}$-octanoyl human insulin analog, a B28-N$^\epsilon$-Arg$^{A0}$Gly$^{A21}$Gln$^{B3}$Lys$^{B28}$Pro$^{B29}$Arg$^{B31}$Arg$^{B32}$-octanoyl human insulin analog, a B28-N$^\epsilon$-Arg$^{A0}$Gly$^{A21}$Asp$^{B3}$Lys$^{B28}$Pro$^{B29}$Arg$^{B31}$Arg$^{B32}$-octanoyl human insulin analog, a B28-N$^\epsilon$-Lys$^{B28}$Pro$^{B29}$Arg$^{B31}$Arg$^{B32}$-octanoyl human insulin analog, and a B28-N$^\epsilon$-Arg$^{A0}$Lys$^{B28}$Pro$^{B29}$Arg$^{B31}$Arg$^{B32}$-octanoyl human insulin analog.

23. A formulation comprising the mono-acylated insulin analog of claim 4, and a preservative.

24. The formulation of claim 23, wherein the preservative is selected from the group consisting of m-cresol and phenol.

25. The formulation of claim 23, further comprising an isotonicity agent.

26. The formulation of claim 23, further comprising a pharmaceutically-acceptable buffer.

27. The formulation of claim 23, further comprising a metal in the +2 oxidation state.

28. The formulation of claim 27, wherein the metal is selected from the group consisting of cobalt and zinc.

29. The formulation of claim 23, wherein the formulation is at a pH between about pH 3.0 and about pH 3.8.

30. The formulation of claim 23, wherein the formulation is at a pH of about 3.5.

31. The formulation of claim 23, wherein the formulation is at a pH between about 4.5 and about 7.6.

32. The formulation of claim 23, wherein the formulation is at a pH between about 5.0 and about 7.0.

33. The formulation of claim 23, wherein the formulation is at a pH of about 6.5.

34. A method of treating diabetes, comprising administering to a patient in need of such treatment, an effective dose of the insulin analog of claim 4.

35. A method of treating diabetes, comprising administering to a patient in need of such treatment, an effective dose of the formulation of claim 29.

36. A method of treating diabetes, comprising administering to a patient in need of such tr eatment, an effectve dose of the formulation of claim 30.

37. A method of treating diabetes, comprising administering to a patient in need of such treatment, an effective dose of the formulation of claim 31.

38. A method of treating diabetes, comprising administering to a patient in need of such treatment, an effective dose of the formulation of claim 32.

39. A method of treating diabetes, comprising administering to a patient in need of such treatment, an effective dose of the formulation of claim 33.

* * * * *